(12) United States Patent
Toews et al.

(10) Patent No.: US 7,308,300 B2
(45) Date of Patent: Dec. 11, 2007

(54) MEDICAL INJECTION SYSTEM

(75) Inventors: Glenn Toews, Eden Prairie, MN (US); Chris Szczech, Clearwater, MN (US); Thomas J. McPeak, Shakopee, MN (US); Douglas J. Duchon, Chanhassen, MN (US)

(73) Assignee: Acist Medical Systems, Inc., Eden Prairie, MN (US)

( * ) Notice: Subject to any disclaimer, the term of this patent is extended or adjusted under 35 U.S.C. 154(b) by 906 days.

(21) Appl. No.: 10/126,799

(22) Filed: Apr. 19, 2002

(65) Prior Publication Data

US 2002/0183616 A1 Dec. 5, 2002

Related U.S. Application Data

(60) Provisional application No. 60/294,471, filed on May 30, 2001.

(51) Int. Cl.
*A61M 5/00* (2006.01)
(52) U.S. Cl. .................. 600/432; 604/247; 604/249
(58) Field of Classification Search .............. 604/82, 604/254, 247, 249, 182–4, 257–9, 89–91; 600/432
See application file for complete search history.

(56) References Cited

U.S. PATENT DOCUMENTS

| | | | | |
|---|---|---|---|---|
| 2,322,753 A | * | 6/1943 | Thomas | ................. 604/83 |
| 3,118,435 A | * | 1/1964 | Almquist | ................. 123/572 |
| 3,731,679 A | | 5/1973 | Wilhelmson et al. | |
| 3,739,943 A | | 6/1973 | Wilhelmson et al. | |
| 4,476,999 A | | 10/1984 | Bilbrey | |
| 4,512,764 A | | 4/1985 | Wunsch | |
| 4,535,820 A | | 8/1985 | Raines | |
| 4,559,036 A | | 12/1985 | Wunsch | |
| 4,854,324 A | | 8/1989 | Hirschman et al. | |
| 4,966,199 A | | 10/1990 | Ruschke | |
| 4,966,579 A | | 10/1990 | Polaschegg | |
| 5,226,886 A | | 7/1993 | Skakoon et al. | |
| 5,249,579 A | | 10/1993 | Hobbs et al. | |
| 5,254,101 A | | 10/1993 | Trombley, III | .............. 604/207 |
| 5,267,964 A | | 12/1993 | Karg | |
| 5,346,470 A | | 9/1994 | Hobbs et al. | |
| 5,494,036 A | | 2/1996 | Uber, III et al. | |
| 5,515,851 A | | 5/1996 | Goldstein | |
| 5,569,181 A | | 10/1996 | Heilman et al. | |
| 5,739,508 A | | 4/1998 | Uber, III | |

(Continued)

FOREIGN PATENT DOCUMENTS

GB 781554 8/1957

(Continued)

*Primary Examiner*—Kevin C. Sirmons
*Assistant Examiner*—Catherine N. Witczak
(74) *Attorney, Agent, or Firm*—Kramer, Levin, Naftalis & Frankel LLP

(57) ABSTRACT

A method of preventing extravasation of contrast agent during a computed tomography injection. An automatic injector device facilitates ease of accomplishing the method. The method includes establishing the absence of extravasation using an absorbable injectate, such as saline, prior to injecting the contrast agent. The device includes a computerized injector head capable of switching between two injectates without physical human intervention. The device is controlled by a remote operating panel located in a control room that is protected from X-ray radiation. The device includes various software driven safety features that prevent the occurrence of unsafe conditions.

20 Claims, 15 Drawing Sheets

U.S. PATENT DOCUMENTS

| | | |
|---|---|---|
| 5,761,414 A | 6/1998 | Akaishi et al. |
| 5,795,333 A | 8/1998 | Reilly et al. |
| 5,806,519 A | 9/1998 | Evans, III et al. |
| 5,808,203 A | 9/1998 | Nolan, Jr. et al. |
| 5,840,026 A | 11/1998 | Uber, III et al. |
| 5,843,037 A | 12/1998 | Uber, III |
| 5,873,861 A | 2/1999 | Hitchins et al. |
| 5,885,216 A | 3/1999 | Evans, III et al. |
| 5,920,054 A | 7/1999 | Uber, III |
| 5,947,935 A | 9/1999 | Rhinehart et al. |
| RE36,648 E | 4/2000 | Uber, III et al. |
| 6,096,011 A | 8/2000 | Trombley, III et al. |
| 6,149,627 A | 11/2000 | Uber, III |
| 6,197,000 B1 | 3/2001 | Reilly et al. |
| 6,212,134 B1 | 4/2001 | Yamashita |
| 6,306,117 B1 | 10/2001 | Uber, III |
| 6,317,623 B1 | 11/2001 | Griffiths et al. ............ 600/431 |
| 6,339,718 B1 | 1/2002 | Zatezalo et al. |
| RE37,602 E | 3/2002 | Uber, III et al. |
| 6,385,483 B1 | 5/2002 | Uber, III et al. |
| 6,397,098 B1 | 5/2002 | Uber, III et al. ........... 600/431 |
| 6,402,717 B1 | 6/2002 | Reilly et al. .................. 604/67 |
| 6,440,107 B1 | 8/2002 | Trombley, III et al. |
| 6,442,418 B1 | 8/2002 | Evans, III et al. |
| 6,471,674 B1 | 10/2002 | Emig et al. |
| 6,475,192 B1 | 11/2002 | Reilly et al. ................ 604/189 |
| 6,520,930 B2 | 2/2003 | Critchlow et al. |
| 6,643,537 B1 | 11/2003 | Zatezalo et al. |
| 6,652,489 B2 | 11/2003 | Trocki et al. ............... 604/154 |
| 6,673,033 B2 | 1/2004 | Sciulli et al. ................. 604/67 |
| 6,699,219 B2 | 3/2004 | Emig et al. ................. 604/131 |
| 6,731,971 B2 | 5/2004 | Evans, III et al. |
| 6,733,477 B2 | 5/2004 | Cowan et al. ............. 604/181 |
| 6,733,478 B2 | 5/2004 | Reilly et al. ................ 604/189 |
| 6,743,202 B2 | 6/2004 | Hirschman et al. ......... 604/131 |
| 6,889,074 B2 | 5/2005 | Uber, III et al. ............ 600/431 |
| 6,901,283 B2 | 5/2005 | Evans, III et al. ......... 600/431 |
| 6,939,302 B2 | 9/2005 | Griffiths et al. ............. 600/458 |

FOREIGN PATENT DOCUMENTS

| | | |
|---|---|---|
| WO | 98/11927 | 3/1998 |
| WO | WO 98/11927 | 3/1998 |

* cited by examiner

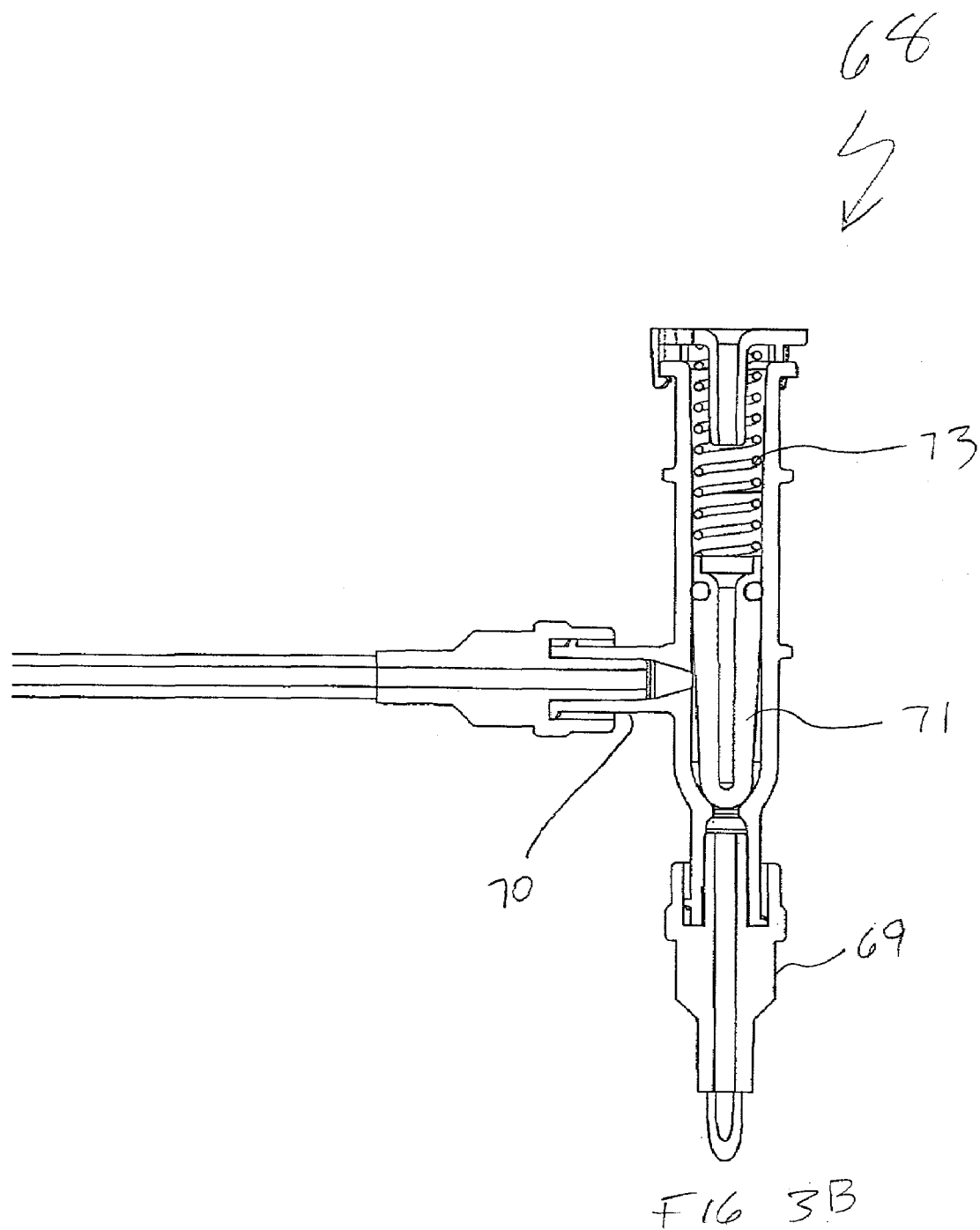

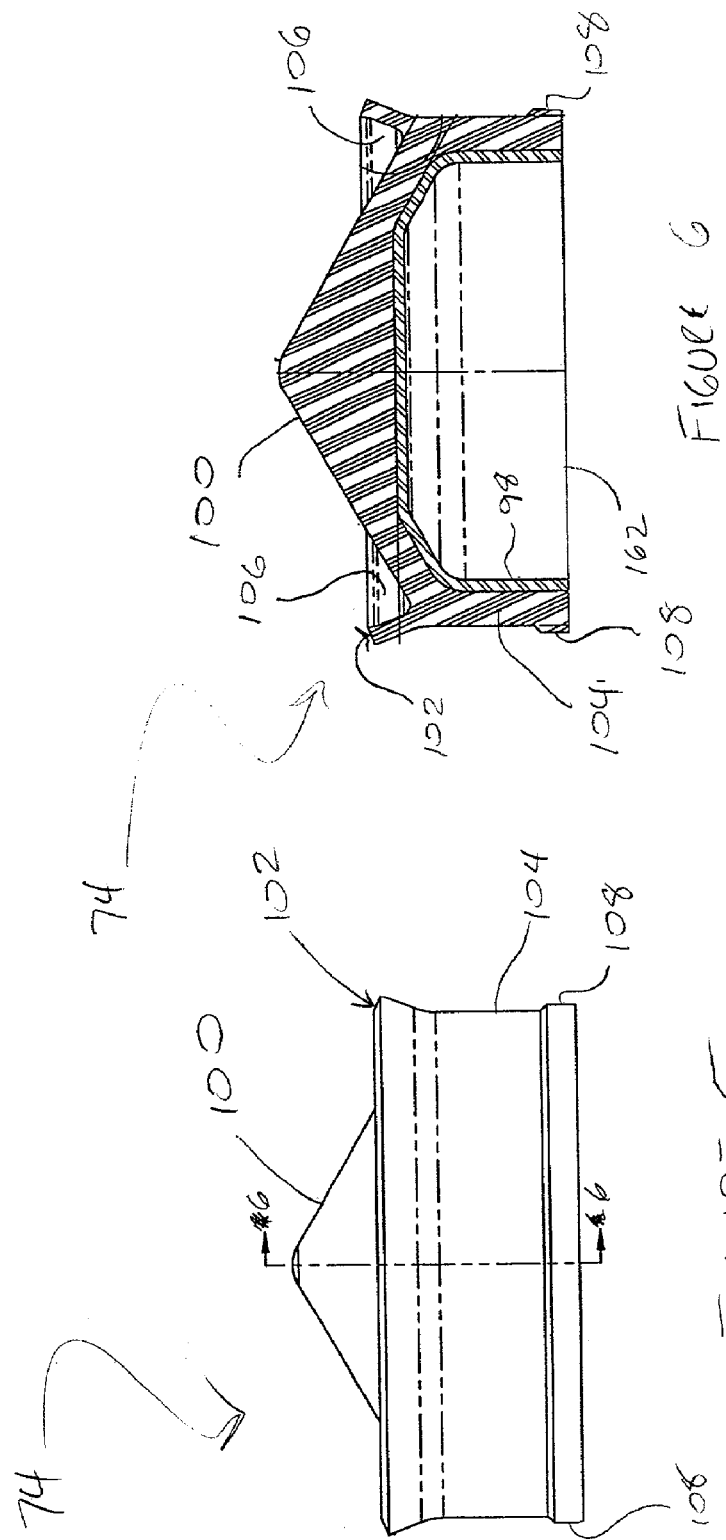

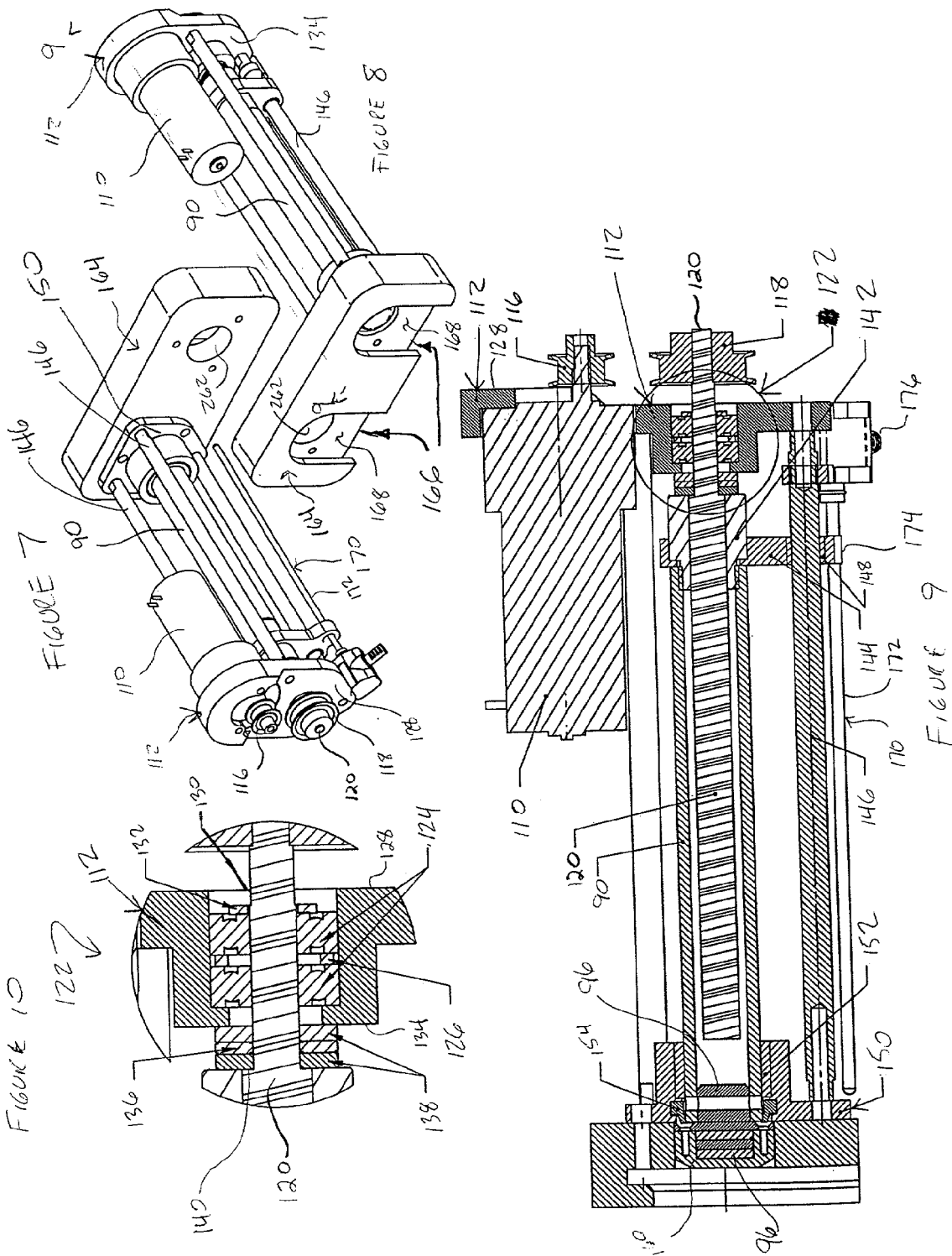

MEDICAL INJECTION SYSTEM

CROSS REFERENCE TO RELATED APPLICATIONS

This application claims priority from U.S. Provisional Application Serial No. 60/294,471 filed on May. 30, 2001 and entitled CT INJECTOR SYSTEM, incorporated by reference herein in its entirety.

BACKGROUND OF THE INVENTION

Computed tomography (hereinafter "CT") is a medical procedure whereby an X-ray imaging machine is used to take cross-sectional images of a patient. The source of the X-rays is placed on one side of the body while an array of detectors is placed on the other side. The X-rays pass through the body and are read by the detectors on the other side. The signals received by the detectors are sent to a computer which compiles the data to create images. The detectors and X-ray source may be rotated around the body, while the body is being translated axially, to create a plurality of layered images.

CT differs from traditional X-ray imaging in that a computer is used to first "record" the image. Often, a contrast agent providing radiopaque contrast is injected into the patient intravenously to greatly enhance the images. Because the nature of CT is more like a continuous "movie" rather than a snapshot-like traditional X-ray, the flow and efficacy of the contrast agent may be monitored during the procedure.

Using radiopaque contrast agents for CT procedures, however, involves complications. For example, extravasation, the unintentional delivery of an injectate into the tissue surrounding the targeted vein or artery, can be a serious complication when injecting a radiopaque contrast agent during a CT procedure. These contrast agents are relatively thick solutions that are not easily absorbed by human tissue. Thus, whereas extravasation of an easily-absorbed solution, such as saline, is of relatively minor consequence, extravasation of a CT contrast agent can be a painful mishap often requiring an invasive, surgical removal procedure called a fasciotomy.

Extravasation occurs whenever the tip of the percutaneous needle is not located in the target vein and injectate is nonetheless delivered through the needle. There are various causes of extravasation. One cause involves a technician or nurse missing the lumen of the target vein, or passing completely through the vein with the needle tip, during introduction. Another cause involves the jetting force of the injectate creating a rearward, resultant force on the needle, pushing the needle out of the vein, or pushing the vein away from the needle tip until the tip is no longer in the lumen. Extravasation may also be caused by the jet force of the injectate eroding through the wall of the vessel.

Manual control of the injection flow rate by a skilled technician would effectively minimize extravasation caused by excessive jetting force. However, as previously mentioned, contrast agent continues to be injected into the vein during a CT procedure. A technician manually injecting the agent would thus be exposed to repeated, and cumulatively harmful, doses of X-ray radiation.

The need for precise control over the flow rate of CT contrast agent, along with the hazards of repeated exposure to X-ray radiation, has illuminated the need for the development of a computer controlled, automatic injector system. The applicants have developed a somewhat similar system for use in angiographic procedures. This system is described in U.S. Pat. No. 6,099,502, filed Oct. 24, 1997, and U.S. patent application Ser. No. 09/542,422, filed Apr. 4, 2000, both of which are incorporated herein by reference in their entireties.

Angiograms are similar to CT scans in that the same contrast agent is used to form an X-ray image. However, angiograms do not share many of the complications of CT scans. Angiograms involve the introduction of a long catheter into the aorta through an entry in the groin. The catheter is threaded through the aorta to the target site, such as the heart or brain, and used to deliver a larger volume of injected contrast agent in a short time. The goal is to create a slug of contrast agent that occupies substantially the entire lumen of the target site in order to form an image of the targeted vascular system. Once the agent is injected, a series of traditional X-rays are taken. If it is determined that more X-rays are needed, another slug of contrast agent is injected. Thus, extravasation is much less likely to happen as the catheter is positioned deep within the aorta and the location of the distal end is established before the agent is introduced. Further, there is sufficient time between the introduction of the agent and the taking of the X-rays for the attending physician and technicians to leave the X-ray room.

The aforementioned injector system was developed because technicians were unable to achieve the necessary injectate flow rate manually. However, this system is unsuitable for CT agent introduction. In addition to being too large, it requires the technician to be present in the X-ray room during operation.

It would be desirable to develop an automated injector system tailored to the unique needs of CT. Such a system would optimally provide remote operation, redundant safeguards against uncontrolled agent introduction, and the ability to alternate between two injectates. A need for a method of injecting a radiopaque contrast agent that reduces the risk of contrast agent extravasation is also needed.

SUMMARY OF THE INVENTION

In one aspect of the present invention, there is a method of injecting a contrast agent that minimizes the extravasation of the agent. The method involves the use of a preliminary injection of an easily absorbable liquid, such as saline, to establish the absence of extravasation.

While the preliminary injection of saline is being administered, the technician monitors the injection site by palpation for signs of extravasation. If extravasation is present, the technician repositions the needle and repeats the process of injecting saline and monitoring for signs of extravasation. Because saline is readily absorbed by the body, the extravasation of saline is much less painful and less likely to cause scarring than the extravasation of contrast. Thus, if extravasation occurs while injecting saline, a fasciotomy is typically unnecessary.

Once it is confirmed that extravasation is not present, the needle or catheter is held in place and fluidly connected to a supply of contrast agent. The contrast agent is introduced at a flow rate that may be approximately equal to that of the saline, thereby minimizing the possibility of extravasation caused by the jetting force of the injectate. Once the desired quantity of contrast agent has been administered, it is preferable to inject a second quantity of saline. Doing so flushes the introduction site of contrast agent, thereby reducing pain and preventing any inadvertent extravasation during needle extraction. Doing so also increases the patency of the contrast agent. It has been determined that providing such a saline boost following the agent allows a smaller dose of the expensive contrast agent to be used without sacrificing image quality. Additionally, this boost injection ensures that the intended dosage of contrast agent is actually delivered to the patient by flushing the remainder of the contrast bolus from the tubing connected to the percutaneous needle.

In order to present an environment in which a patient may receive a CT agent while being exposed to X-ray radiation, without the need for an attending technician, another aspect of the present invention is an automatic injector system. The system includes a remote operating panel which may be located in a radiation-free control room, adjacent to the room where the patient is located. The system generally comprises a mechanical linear actuator controlled by a computerized operating system. The linear actuator is operably connected to a plunger within a syringe to either force fluid from the syringe or draw fluid into the syringe. An operating system controlling the automatic injector system is enabled by software programs that allow a technician to input flow rates and quantities.

The linear actuator includes a plunger rod that is preferably magnetically coupled to the plunger. A magnetic coupling between the plunger rod and the plunger is advantageous over a traditional "snap fit" connection, commonly used in other automatic injector devices. This "snap fit" arrangement is found on systems wherein automatic engagement and disengagement of the plunger with the plunger rod is desirable to prevent contaminating the syringe pumping chamber and to simplify the operation of the injector system. In some situations, it is desirable to damage or destroy the connection portion of the plunger to prevent syringe reuse. As a result of the unsnapping and/or destruction of the connection, particles may remain in the connection area and cause problems during subsequent interconnections. Magnetically coupling the actuator to the plunger provides a connection which is broken cleanly and, lacking interlocking componentry, is not susceptible to clogging or other interference.

Another advantage of providing a magnetically coupled, actuator-plunger relationship is that a connection is established without requiring any connection force. One problem often encountered with automatic injectors using snap connections is that the force necessary for engagement is too high, while the force necessary for disengagement is too low. With snap connectors it may be difficult to maintain the plunger in a fixed position relative to the pumping chamber because the plunger may be driven forward during the engagement procedure. Additionally, it may be difficult to maintain the plunger in an engaged position with the plunger rod when the plunger rod is retracted. Instances where a connection is either never achieved, or not achieved until the plunger has reached the distal end of the syringe, are not uncommon. A magnetized plunger rod connects to a ferrous or magnetic plunger coupling with a zero, if not a negative, connection force.

Preferably, the magnetic connection employs rare earth neodymium iron boron magnets. Rare earth magnets are strong enough and small enough to maintain contact with the plunger while the plunger is being withdrawn to draw fluid into the syringe. A stack of such magnets may be used to increase the power of the magnetic field.

The performance of the magnetic connection is further enhanced by using an advanced plunger design with the syringe. The plunger includes a lip seal that prevents fluid within the syringe from leaking out, prevents contaminants and air from entering the syringe, and assists the gripping power of the magnets by reducing the friction between the inner walls of the syringe and the sides of the plunger. A thin ridge or lip is oriented radially outward and is angled forward from the leading edge of the side of the plunger. Upon the application of force from the injector actuator to the plunger assembly, the fluid pressure within the syringe increases. This increase in pressure forces the lip into closer contact with the internal surface of the syringe bore. The contact force between the lip and the syringe bore is directly proportional to the fluid pressure, reinforcing the seal between these surfaces with increasing pressure.

This lip seal may be used in combination with standard seal "bumps" that protrude radially around the circumference of the plunger assembly. A second lip seal, rearward of the first lip seal and angled rearward rather than forward, may be used to more effectively prevent the ingress of air into the syringe bore when the plunger is being withdrawn during a fill operation.

Notably, the existence of one or more of these lip seals greatly reduces the area of contact between the plunger and the bore compared to more conventional syringe designs. This reduction in contact area corresponds to a reduction in friction and thus enhances the performance of the magnetic connection between the plunger rod and the plunger.

Another aspect of the present invention provides an injectate delivery device that enables a technician or automated injector to easily switch between two different solutions using a common percutaneous introducer such as a needle or catheter. The device is preferably constructed and arranged for insertion into the aforementioned automatic injector system.

In one aspect of the delivery device, there are provided two separate syringes fluidly connected to the percutaneous needle or catheter with a fluid communications network. The network has one or more valves directing the fluid toward the lumen of the needle or catheter. This device reduces the possibility that the needle or catheter will be inadvertently displaced from the target vein when switching injectates.

Preferably, the device further includes connections to fluid supplies, and associated valves, such that one syringe may be filled with a liquid without affecting the operation of the other syringe. This device may be embodied using material that will result in a disposable, single-use device, or using a combination of materials such that portions of the device are reusable.

The valve network provided with the various embodiments of the injectate delivery device is constructed and arranged to automatically port a pressurized liquid to the introducing catheter. Manually actuated valves are either minimized or completely replaced, thus eliminating the potential for operator error and allowing the fluids to be alternated remotely.

Alternatively, there is provided a similar delivery device that provides only one syringe. Similar in design and construction to the two-syringe embodiment, this less expensive embodiment is ideally situated to applications where only one injectate is necessary. If necessary, this embodiment may be used to alternate injectates by switching the supply reservoir from which the device is drawing injectate.

Another aspect of the automatic injector system is a computerized operating system. The computerized operating system includes a remote operating panel located in an adjacent room, shielded from X-ray radiation. Because the present invention pertains to a computerized machine performing a medical procedure in the absence of immediate human contact, redundant safety measures are needed. A variety of safety features are thus incorporated into the present invention to preserve, or improve upon, the standards of safety exercised when contrast agents are injected manually.

The present invention includes components located in the vicinity of the patient, and remote components, located in an adjacent control room, that are used by physicians to operate and monitor components in the patient room. In addition to the components described above, the patient room also includes an injector head. As used herein, "injector head" generally refers to a computer controlling a motor connected to a linear actuator or plunger rod. As mentioned above, the linear actuator is operably attached to the plunger such that the plunger may be moved back and forth within the syringe. In the embodiment providing two syringes, the injector head preferably includes two motors and two linear actuators, controlled by the computer. Alternatively, the injector head includes one motor alternatingly engageable to two linear actuators.

The components in the control room include a monitor, such as a liquid crystal display (LCD) touch monitor, and a computer with a power supply. The computer communicates with and controls the injector head from the control room. Having introduced the basic components of the system, it is now possible to briefly summarize the basic safety features relating to the injector head of the present invention.

One aspect of the injector head of the present invention includes a watchdog computer program for ensuring all safety-critical computer programs or "tasks" that are supposed to be running during an injection operation are doing so without error. Computer-controlled, safety-critical medical devices must ensure that if the computer processor becomes inoperable for any reason, the system can be shut down in a manner that will not harm the patient or operators of the device. Electronic watchdog circuits that require the software to signal the watchdog circuit at a predetermined time interval are known. However, in a multitasking operating environment, it is possible that the task responsible for signaling the watchdog circuit remains operational while a separate task pertaining to patient safety becomes inoperable in a manner undetected by the electronic watchdog circuit. Thus, this watchdog program includes a code segment that monitors signals from each of the safety-critical tasks, either by passively receiving "operation normal" signals from the tasks, if they are so programmed to send these at predetermined intervals, or by requesting or pulling such signals from the tasks. The program also includes a code segment that verifies that such an "operation normal" signal has been received from each and every one of the designated safety-critical tasks. In other words, the program repeatedly performs a "roll call" at a predetermined interval.

This code segment, herein referred to as the "watchdog task" then sends a reset signal to a watchdog timer code segment. The watchdog timer code segment is a timer that runs continuously, beginning from zero, whenever it is reset. A shutdown code segment sends a shutdown signal to a motor shutdown logic circuit, discussed below, whenever the timer reaches a predetermined elapsed time. Thus, the watchdog computer program generates a shutdown signal unless it is verified that each of the safety tasks is operating normally during the predetermined interval.

One of the critical safety tasks monitored by the watchdog task is an interprocessor communications link task run by the microprocessors of the injector head and the remote operating panel. The two microprocessors communicate with each other via an acceptable communication link. The processors send messages to each other at predetermined intervals, verifying that they are operating normally. When it is established that the processors are operating normally, an operation normal signal is sent to the watchdog task, as described above.

Another aspect of the injector head of the present invention is a safety circuit that includes the aforementioned motor shutdown logic circuit. This safety circuit provides a degree of redundancy to the watchdog computer program. A plurality of comparators, each having a first input line, a second input line, and an output line are provided. The first input line of each comparator receives a voltage signal from a sensor measuring a selected operating parameter of the automatic injector system. Examples of such parameters include: plunger speed, plunger position, and motor torque, for both the saline and the contrast agent plungers and/or motors.

The second input line is preferably connected to a digital-to-analog converter which takes an inputted limit on one of the parameters, converts it to an analog signal, and sends it to the comparator. The comparator compares the signal from the first line to that of the second line. If the difference exceeds a predetermined threshold, the comparator sends a signal to the motor shutdown logic circuit. Thus the motor logic circuit is able to receive signals from any of the comparators and from the watchdog timer. The motor logic circuit is also connected to a relay electrically connecting the motor of the injector head to a power supply. The motor logic circuit is designed to trip the relay when it receives a signal from any of the comparators or the shutdown code segment.

Another safety feature of the injector head includes a computer program to control the flow rate created by the plunger being forced through the syringe by the motor. The computer program is embodied on a computer readable medium executable by a computer and generally comprises a velocity loop and a pressure loop. The velocity loop is a code segment capable of comparing data representative of actual plunger speed to a predetermined speed setting. The pressure loop is a code segment capable of comparing data representative of actual motor load to a predetermined motor load limit.

The velocity loop and the pressure loop work together to ensure the safe delivery of the contrast agent and/or saline to a patient. The velocity loop maintains the flow rate of the fluid within a predetermined range so that the contrast agent flow rate is high enough to be effective, but not excessive causing internal trauma, such as extravasation. The pressure loop monitors the load on the motor, becomes active at a selected setting, and prevents the load from exceeding the selected setting by a predetermined amount. Motor load is representative of pressure on the plunger. If a blockage were to occur in the fluid path, for example, the flow rate could be decreased. The velocity loop would note that the plunger speed has decreased and would send a signal to increase the motor speed. However, the presence of the blockage would result in an increased load condition on the motor, and an increase in pressure within the syringe. The pressure loop thus either shuts the system down or slows the motor speed if the motor load exceeds the selected setting by a predetermined amount. These loops are preferably software programs but may be solid state circuits or even mechanical feedback devices.

Because the automatic injector is driven by at least one microprocessor, the system must be capable of storing the data and software used for executing the application. It would be desirable to have the capability to install software after the device has been assembled. This capability facilitates ease of manufacture and allows immediate field upgrades without significant down time. Thus, it is preferable to provide the software and data storage capability on a modular memory card, such as CompactFlash™. The CompactFlash™ mass storage device is a card which can be unplugged and replaced through an access point on the injector device. Using a CompactFlash™ removable mass storage device for storing application software, calibration data, and device usage data, provides the ability to both download and retrieve the software and data from the injector using a connected computer, and to physically remove and replace the CompactFlash™ card with the data on it.

The microprocessor may be configured for connection to the Internet or an intranet, thereby allowing a physician in a remote location to program various injector parameters. Remote connectivity could also be used for manufacturer troubleshooting without requiring a technician to make an on-site service call.

BRIEF DESCRIPTION OF THE DRAWINGS

FIG. 3b is a plan cutaway view of the catheter connector of the present invention;

FIG. 5 is an elevation view of a plunger of the present invention;

FIG. 6 is a section view of the plunger of FIG. 5 taken generally along lines 6-6;

FIG. 7 is a rear perspective view of a linear actuator assembly of the present invention;

FIG. 8 is a front perspective view of a linear actuator assembly of the present invention;

FIG. 9 is a side elevation sectional view of the linear actuator assembly of FIG. 8 taken generally along lines 9-9;

FIG. 10 is an enlarged view of the circled area bearing assembly 122 of FIG. 9;

DETAILED DESCRIPTION OF THE INVENTION

Method of Preventing Extravasation

Figure 1:
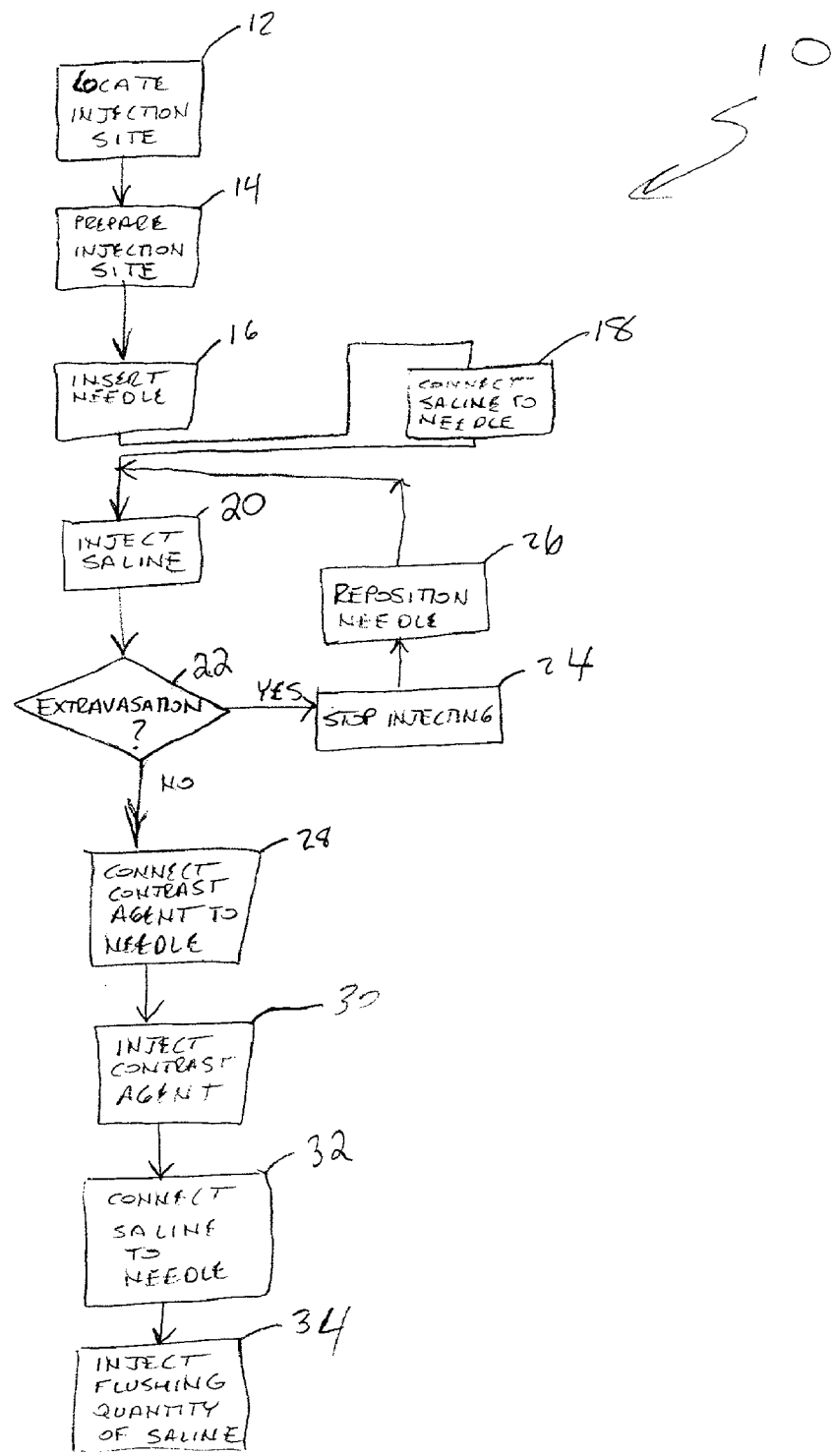
FIG. 1 is a flow chart that describes a method of preventing contrast agent extravasation of the present invention.

FIG. 1 shows a flow diagram of the method of preventing extravasation 10 of the present invention. Beginning at 12, an injection site is located by the attending health professional and prepared for injection at 14 using appropriate cleaning techniques. The needle or catheter is inserted at 16 to establish fluid communication between the needle or catheter and the targeted lumen of the patient.

At 18, a supply of saline is fluidly connected to the needle or catheter and, at 20, a quantity of saline is injected into the patient at a predetermined flow rate that may be approximately equal to the desired flow rate of the eventual contrast agent injection. It is preferred that the flow rate of the saline injection be at least as great as the planned flow rate of the contrast agent. Doing so ensures that extravasation complications caused by jetting forces will be revealed prior to the introduction of the contrast agent. While the saline is being injected, the attending professional is constantly monitoring by palpation, and visually, at 22. If extravasation is suspected, the professional halts the injection at 24 and repositions the needle at 26. The process then repeats back to step 20 whereby saline is injected and palpation is resumed at 22.

If extravasation is not detected at 22, the attending professional aligns or connects the radiopaque contrast agent to the needle or catheter at 28. At 30, the contrast agent is injected at the preferred flow rate. The flow rate of the contrast agent is chosen for maximum contrast effect. The flow rate of the saline is chosen based on the flow rate of the agent. While contrast agent is being injected, and imaging is occurring, the attending professional preferably leaves the patient room to minimize his or her exposure to radiation.

Upon completion of the contrast agent injection at 30, the saline supply is again connected to the needle or catheter at 32. At 34, a quantity of saline is injected in order to clear the needle, flush the contrast agent away from the injection site, and increase the efficacy of the contrast agent.

Automatic Injector System

The present invention includes an automatic injector system that greatly enhances the method 10, described above. The method 10 included two steps, 28 and 32, where the inserted needle or catheter had to be connected to different fluids. The automatic injector system of the present invention allows this realignment to be performed remotely. The system also provides precise control over the flow rate at which the injectates are administered.

Figure 2:
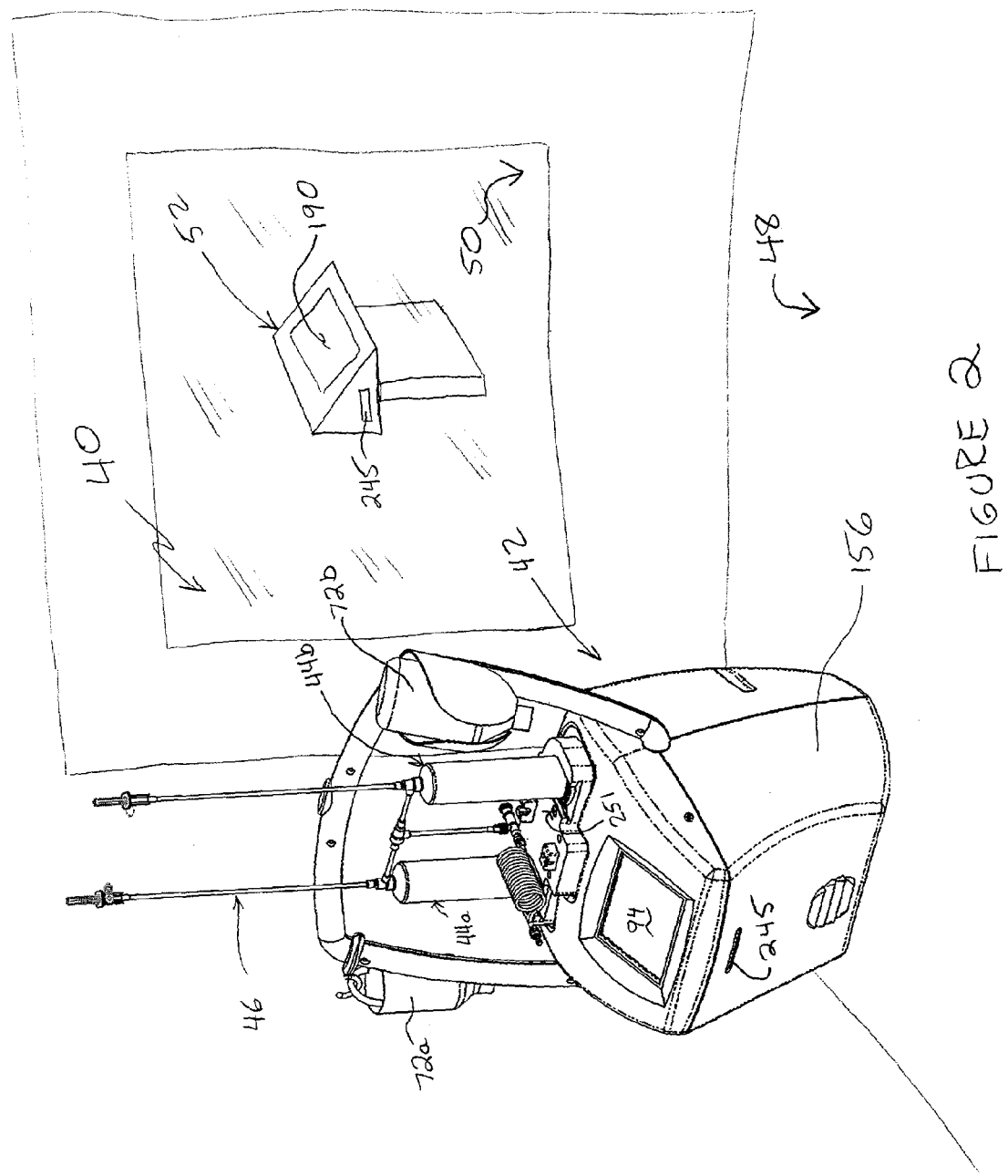
FIG. 2 is a perspective view of an automatic injector system of the present invention.

Referring now to FIG. 2, there is shown a preferred embodiment of the automatic injector system 40 of the present invention. The system 40 generally includes an injector head 42 operably attached to at least one, preferably two, syringes 44. The syringes are attached to a fluid communications network 46. All of the aforementioned components are located in the patient room 48. In an adjacent control room 50, the system 40 also includes a remote operating panel 52. Each of these components will now be discussed in detail.

Syringes and Fluid Communication Network

Figure 3A:
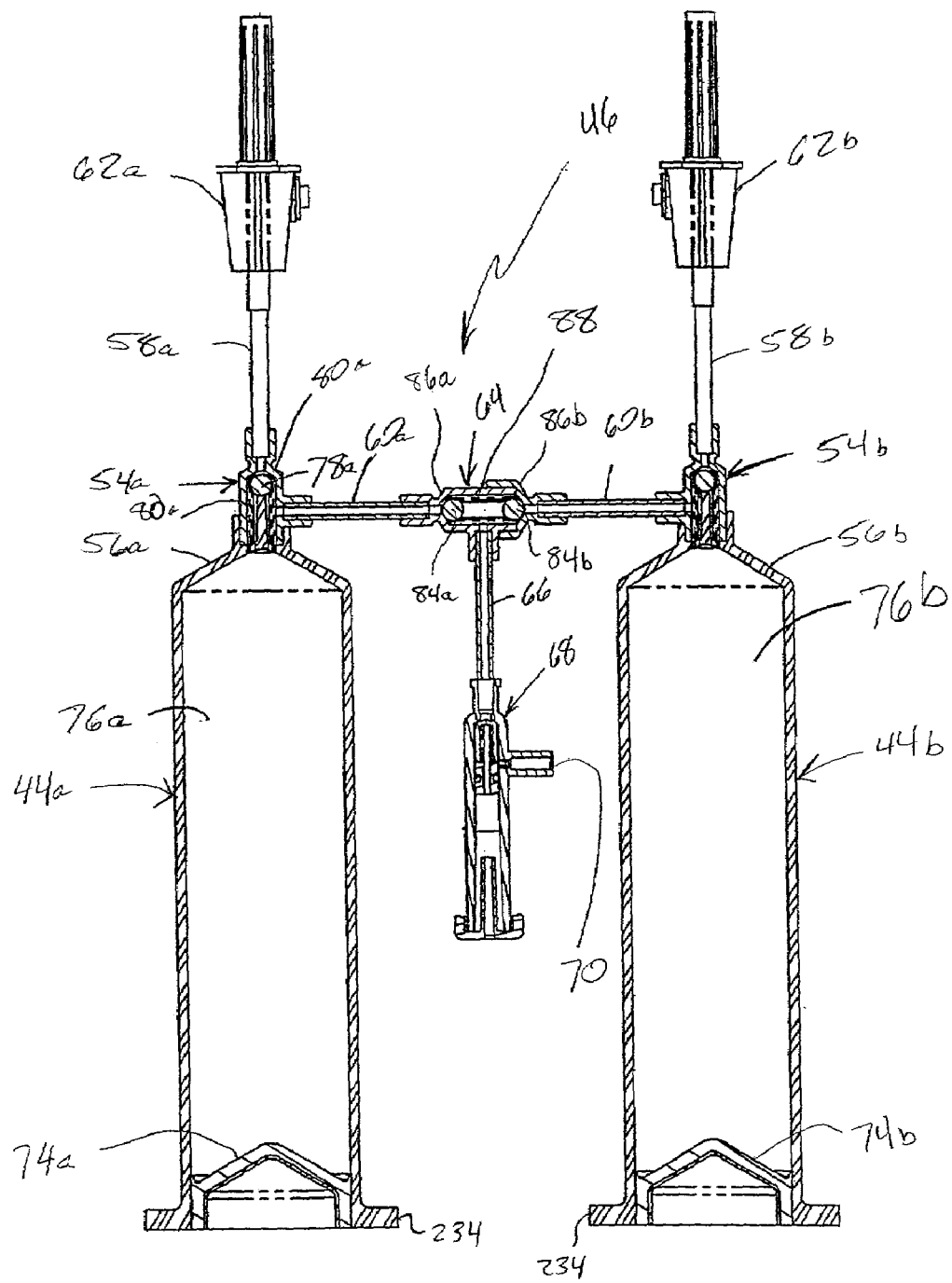
FIG. 3a is a plan cutaway view of the syringes and fluid network of the present invention.
Figure 3C:
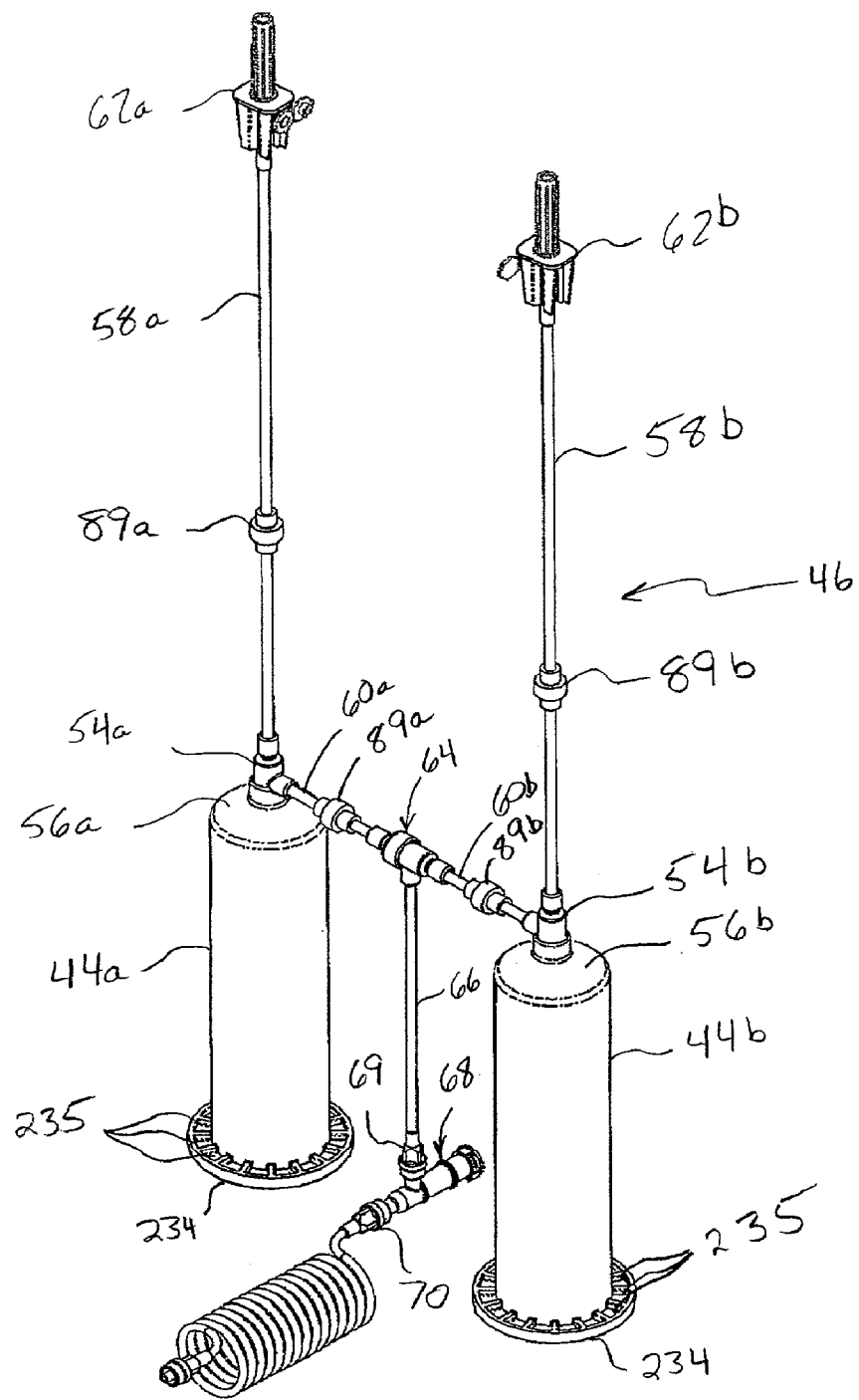
FIG. 3c is a perspective view of a preferred embodiment of the syringes and fluid network of the present invention.

The syringes 44 are connected to the patient with the fluid communication network 46, as best shown in FIGS. 3a-3c. The fluid communications network 46 is a series of valves and tubes. Syringe connector valves 54 connect the distal ends 56 of the syringes 44 to both supply tubes 58 and to cross tubes 60. The supply tubes 58 lead to supply connectors 62 and the cross tubes 60 lead to a common shuttle valve 64. The shuttle valve 64 is a three-way valve allowing fluid to flow from either cross tube 60 into a common tube 66. The common tube 66 leads to a catheter connector 68, which is designed to be attachable to a standard catheter via a port 70. Additionally, the catheter connector may have a medicament port (not shown) that provides a site for injecting fluids other than saline and contrast agents. This medicament port may also be used as an attachment point for an air column detector.

FIG. 3b shows the catheter connector 68 in greater detail. A coupling 69 removably couples the connector 68 to the common tube 66. A plug 71 biased closed by a spring 73 allows fluid flow in only one direction by requiring the pressure created by the syringe 44 to overcome the force of the spring 44.

The supply connectors 62 are attachable to containers 72 (FIG. 2), one of which preferably contains saline and the other preferably contains contrast agent. Because the two-syringe system is designed to allow an attending professional to remotely alternate between the injection of saline and a contrast agent, for ease of explanation, the components carrying saline are labeled "a", and the components carrying contrast agent are labeled "b", throughout the Figures.

The container 72a, then, contains a supply of saline solution. The saline solution is loaded into the syringe 44a by pulling the plunger 74a away from the distal end 56a, thereby creating a negative pressure within the syringe chamber 76a. A close look at the syringe connector valve 54a reveals a plug 78a held in place against a shoulder 80a by a biasing mechanism, preferably a spring 82a. Alternatively, the plug 78a is buoyant, such that the buoyancy of the plug constitutes the biasing mechanism. When the negative pressure created in the syringe chamber 76a is sufficient to overcome the force of the spring 82a, the plug 78a is pulled toward the syringe 44a, compressing the spring 82a, and allowing the saline to flow between the plug 78a and the shoulder 80a and into the syringe chamber 76a. Once the syringe 44a is filled with a sufficient quantity of saline, the plunger 74a is stopped, thereby causing the negative pressure created in the chamber 76a to subside as the saline continues to fill the chamber 76a. The spring 82a quickly overcomes the effects of the negative pressure, and reseats the plug 78a against the shoulder 80a.

When the saline in the chamber 76a is to be injected into the patient, the plunger 74a moves toward the distal end 56a of the syringe 44a, creating a positive pressure in the chamber 76a. The plug 78a prevents the saline from reentering the supply tube 58a. The saline instead is forced into the cross tube 60a toward the shuttle valve 64.

The shuttle valve 64 also uses a plug and shoulder arrangement. To accept fluid from either the saline supply tube 60a or the contrast agent supply tube 60b, the shuttle valve has a plug 84a on its saline side which acts against a shoulder 86a, and a plug 84b on its contrast agent side which acts against a shoulder 86b. The two plugs 84a and 84b are held apart by a spring 88. The shuttle valve 64 connects the two cross tubes 60a and 60b to the common tube 66. Note that the shuttle valve 64 is designed to insulate the common tube from any negative pressure forces arising in the cross tubes 60 when either of the syringes 44 are being filled.

Continuing with the saline injection explanation, when the saline is forced into the cross tube 60a with sufficient pressure to overcome the spring 88, the plug 84a is displaced from the shoulder 86a and the saline is allowed to pass around the plug 84a. The saline, however, is blocked from passing around the other plug 84b, which is seated, now with even greater force, against its respective shoulder 86b. Thus the saline is forced into the common tube 66, through the catheter connector 68 and into the patient via the needle or catheter.

The construction of the components on the contrast agent side of the fluid network 46 are virtually identical to those on the saline side, just described. The design of the syringe connector valves 54 and the shuttle valve 64 allow both syringes to be filled simultaneously and allow fluid from either syringe 44 to be injected alternately without requiring any alignment adjustments. The valves are aligned automatically based on the fluid forces in the network 46.

The fluid network 46 preferably includes a plurality of connectors 89 (FIG. 3c). These connectors are placed between the various other components and allow the components to be replaced and rearranged. For example, the connectors 89a and 89b on either side of the shuttle valve 64 can be used to replace the shuttle valve 64 with a mixing valve (not shown) useable to mix the fluids from the two syringes 44 together. Additionally, the connector 69 can be used to disconnect the network 46 from one patient and use it on another patient without presenting sterility issues.

Injector Head

Figure 4:
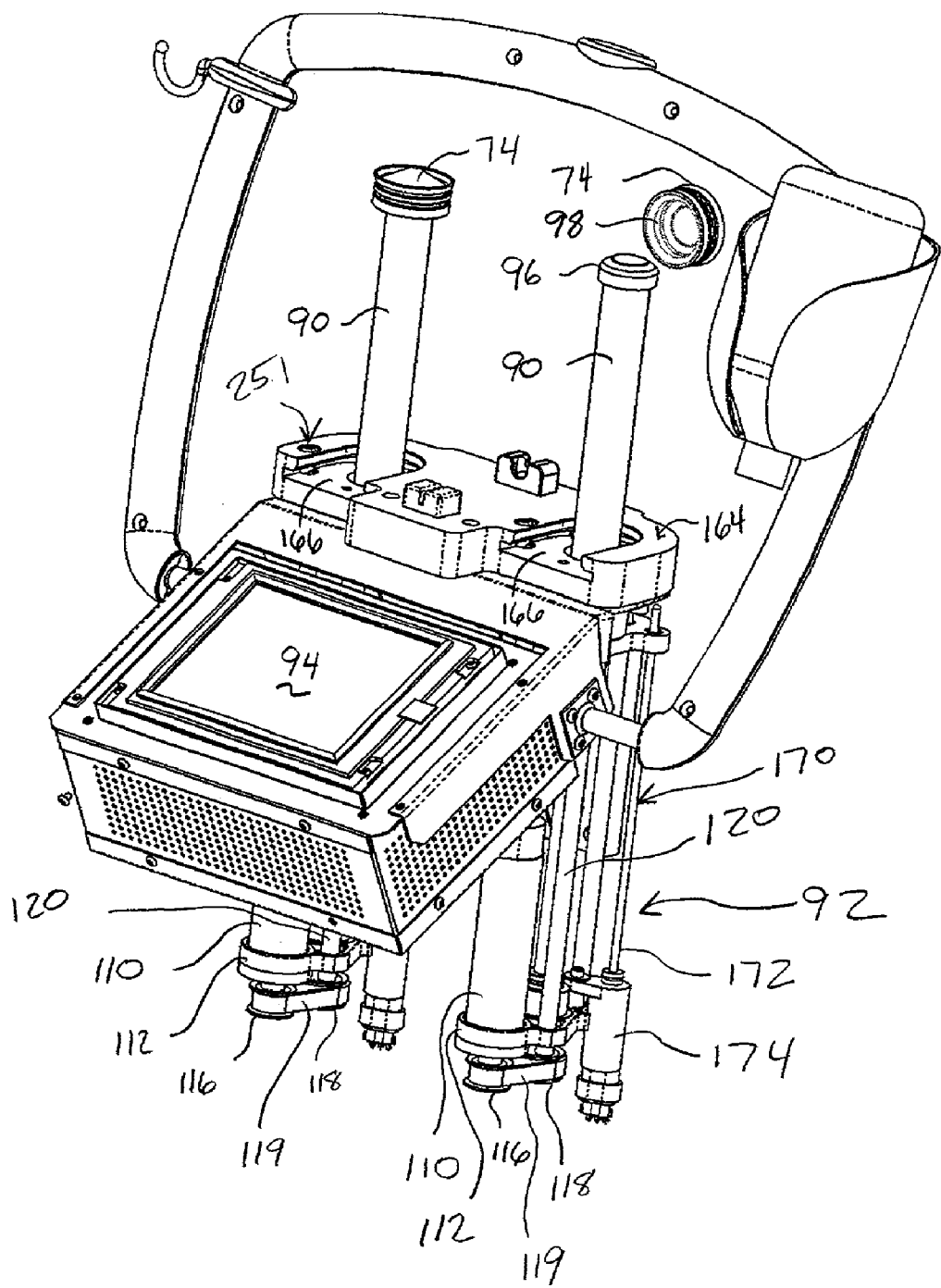
FIG. 4 is a plan view of an injector head of the present invention.

Referring to FIG. 4, the injector head 42 includes one plunger rod 90 per syringe 44, an actuator assembly having one or more motors 110 arranged to move the plunger rods 90, and a local control panel 94. Each plunger rod 90 is connected to the plunger or wiper 74 of the syringe 44. Preferably, the plunger rod 90 includes a magnet or magnetic stack 96 at its distal end that magnetically connects the plunger rod 90 to a ferrous metal insert 98 in the dry side of the plunger 74. Using a magnetic connection between the plunger rod 90 and the plunger 74 is advantageous because it exerts no resistive force when a connection is being made. Neodymium iron boron (NIB) magnets, also known as rare earth magnets, provide sufficient strength to remain attached to the ferrous metal insert 94 when drawing a negative pressure on the syringe 44 during filling. A greater magnetic field may be obtained by using a stack of such magnets.

The performance of the connection between the magnet 96 and the ferrous metal insert 98 is enhanced by the design of the plunger 74. FIGS. 5 and 6 show a preferred plunger 74. The plunger 74 has a conical end 100 that substantially matches the shape of the distal end 56 of the syringe 44. The plunger 74 also has an annular lip 102 angled forward that extends from the sidewall 104 of the plunger in both a forward and an outward direction. The lip 102 is shaped to create an inner surface 106 against which fluid pressure can act to press the lip 102 against the inner sidewall of a syringe 44, thereby improving the seal between the syringe and the plunger. This improved seal reduces the amount of friction between the plunger 74 and the syringe 44, thereby enhancing the performance of the connection between the magnet 96 and the ferrous metal insert 98. Friction is further reduced by providing a rear ridge 108. This ridge 108 also acts against the inner wall of the syringe 44, thereby ensuring that the plunger 74 remains centered within the syringe 44 and also prevents air from seeping past the annular lip 102 when the plunger 74 is being withdrawn, such as when the syringe 44 is being filled. The ridge also prevents the entire sidewall 104 from contacting the inner wall of the syringe 44, thus reducing the friction between the plunger 74 and the syringe 44. It may be desired to provide a ridge 108 which has the same shape as the lip 102, and faces rearward, to further enhance the seal between the ridge 108 and the syringe 44 when the plunger is being withdrawn.

Each of the plunger rods 90 is moved by a linear actuator assembly 92. FIGS. 7-10 present detailed views of the linear actuator assemblies 92. The assembly 92 converts rotational motion from the motor 110 into linear motion imparted to the plunger rod 90. The motor 110 is mounted on a rear plate 112. The shaft 114 of the motor 110 is attached to a motor gear 116 that is rotatably connectable to a plug screw gear 118 with a pulley, belt 119, reduction gear or the like. The plug screw gear 118 is fixed to a plug screw 120 and imparts rotation thereto.

The plug screw 120 is supported by a bearing assembly 122, the details of which are shown in FIG. 10. The bearing assembly 122 also prevents the plug screw from moving axially, relative to the rear plate 112. On the external side 128 of the rear plate 112, the bearing assembly 122 preferably includes a pair of angular contact bearings 124 separated by a spacer washer 126, all held in place against the external side 128 of the rear plate 112 by a lock nut 130 and a lock nut washer 132. On the internal side 134 of the rear plate 112, the bearing assembly 122 includes an axial bearing 136 surrounded by two axial bearing washers 138. One of the axial bearing washers 138 acts against the internal side 134 of the rear plate 112 while the other axial bearing washer 138 acts against a shoulder 140 of the plug screw 120.

The plug screw 120, thus rotates with the motor 110. To impart linear motion to the plunger rod 90, the plug screw 120 is threaded and carries a plug nut 142 that is attached to the plunger rod 90. The plug nut 142 is attached to a guide flange 144 that slides along a tie rod 146 by way of a guide flange bearing 148. The tie rod 146 prevents the plug nut 142 and guide flange 144 from rotating with the plug screw 120, thereby forcing linear movement as the internal threads of the plug nut 142 necessarily interact with the external threads of the plug screw 120. The tie rod 146 is preferably one of four tie rods 146 that connect the rear plate 112 to a front plate 150.

The rearward end of the plunger rod 90 is attached to, and supported by, the plug nut 142. Near the front plate 150, the plunger rod 90 is supported by a linear bearing 152 that is attached to the front plate 150. The plunger rod 90 slides through the linear bearing 152 as the rod 90 linearly advances and returns. In addition to the linear bearing 152, the plunger rod 90 also slides through a rod wiper seal 154, which is forward of the linear bearing 152, and prevents dust from being picked up by the plunger rod 90 while in a forward position, from entering the housing 156 (FIG. 2) of the linear actuator assembly.

The plunger rod 90 is hollow and surrounds the plug screw 120. The forward end of the plunger rod 90 contains the magnet or magnetic stack 96 that is secured to the end of the rod 90 with an end plug 158. The stack is contained within a thin ferrous end cap 160 that is shaped to be received by the dry side 162 of the plunger 74, best seen in FIG. 6. The dry side 162 of the plunger is lined with the ferrous metal insert 98 that is configured to mate with the end cap 160.

Referring again to FIGS. 7-9, it is shown that the front plate 150 is mounted to a docking plate 164. The docking plate 164 includes two receiving grooves 166 for receiving the syringes 44. Note the docking plate 164 is arranged to accept two linear actuator assemblies 92.

The plunger rod 90 is sized such that when it is in the fully retracted position, as shown in FIG. 9, the forward end of the end cap is flush with the back face 168 of the receiving groove 166. This allows a fresh syringe 44 to be slid into place prior to a procedure or midway through a procedure, if necessary. Securing the syringes 44 to the docking plate 164 by sliding them into place, instead of screwing or otherwise twisting them into place, is preferred because any twisting motion imparted to the syringe may twist the fluid communication network 46. Locking the syringes 44 into the grooves 166 is accomplished with a syringe lock assembly 250.

Figure 15A:
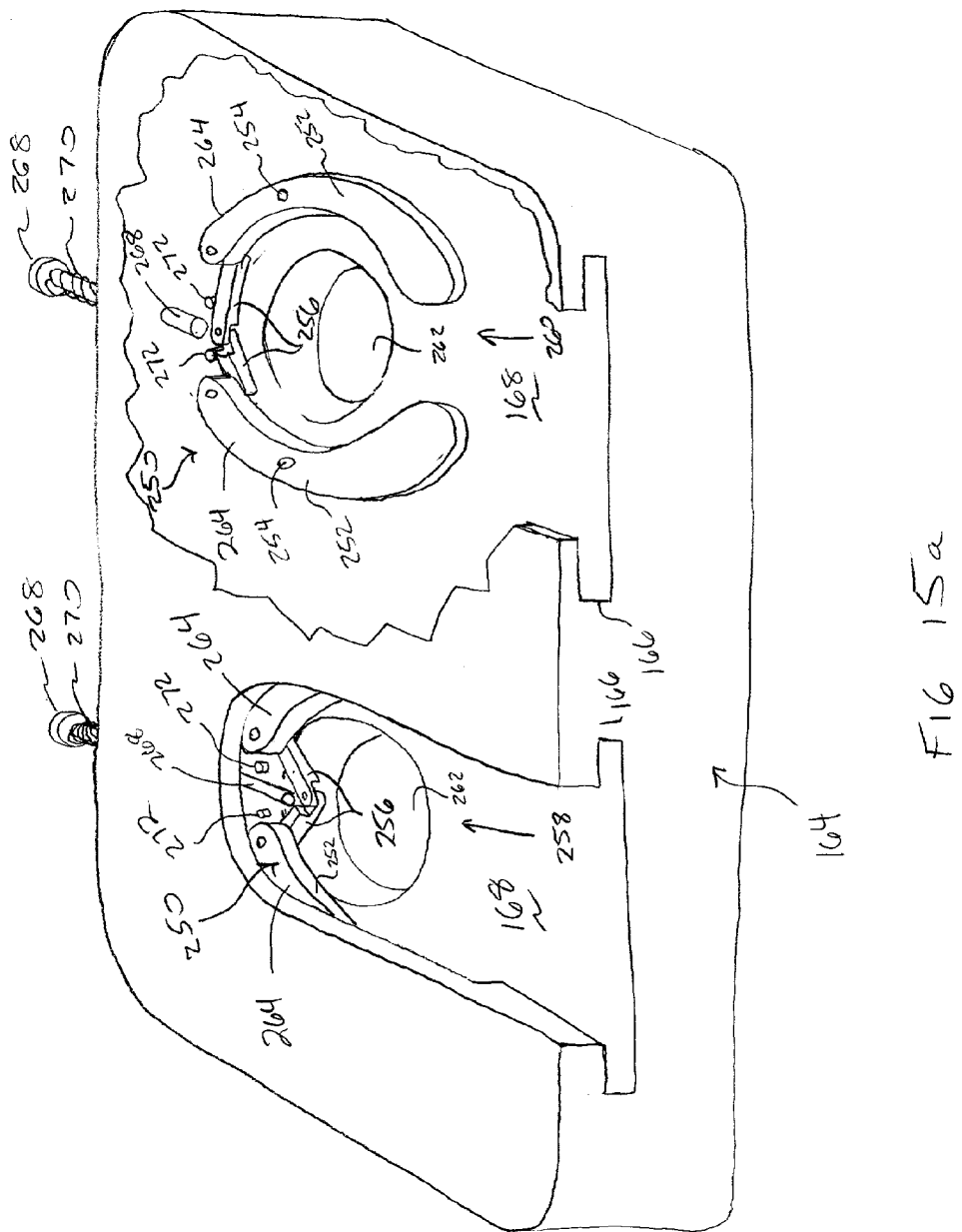
FIG. 15a is a perspective cutaway view of a docking plate equipped with a syringe lock assembly of the present invention.

One embodiment of the syringe lock assembly 250 is best shown in FIG. 15a. The lock assembly 250 includes two engagement members 252 pivotally attached to the docking plate 164 with pivot pins 254. The engagement members 252 are spaced apart from the back face 168 of the docking plate 164 such that the flange 234 of the syringe 44 (FIGS. 3a and 3b) is held between the engagement members 252 and the back face 168. Preferably, the flange 234 includes a plurality of détentes 235 to add rigidity and strength to the flange 234. The engagement members 252 are connected together with linkages 256. The linkages 256 serve to move the engagement members 252 around the pivot pins 254 from an open position 258 to a locked position 260. In FIG. 15, the syringe lock assembly 250 on the left is shown in the open position 258 while the syringe lock assembly 250 on the right is shown in the locked position 260.

Looking at the syringe lock assembly 250 in the open position 258, it can be seen that the linkages 256 fold inward, partially occluding the hole 262 in the docking plate 164, through which the plunger rod 90 passes. When the syringe 44 is slid into the groove 166 and over the hole 168, the flange 234 of the syringe 44 passes under the engagement members 252 and eventually contacts the linkages 256. The flange 234 pushes the linkages upward, forcing the upper portions 264 above the pivot pins 254 apart, thus causing the lower portions 266 below the pivot pins 254 together. The engagement members 252 are shaped such that when the lower portions 266 come together, the engagement members 252 substantially surround the syringe 44, above the flange 234, thereby holding the syringe 44 in place. Furthermore, when fully engaged, the linkages 256 pass slightly beyond alignment with each other, thereby creating an affirming snap engagement into the locked position 260. One or more stops 272, attached to either the docking plate 164 or integral with the linkages 256, prevent the linkages 256 from travelling past alignment to the extent that the linkages 256 begin to pull the upper portions 264 of the engagement members 252 together.

A release pin 268 passes through the docking plate 164 and engages the linkages 256 when the pin 268 is pressed. Depressing the pin 268 moves the linkages 256 downward, pulling the upper portions 264 of the engagement member 252 together, and forcing the lower portions 266 apart. The pin 268 also pushes the linkages 256 into the flange 234 of the syringe 44, thereby forcing the syringe 44 out of the syringe lock assembly 250. A biasing mechanism, such as a spring 270, biases the pin 268 toward an inactive position, thereby preventing an accidental disengagement of the syringe 44.

Figure 15B:
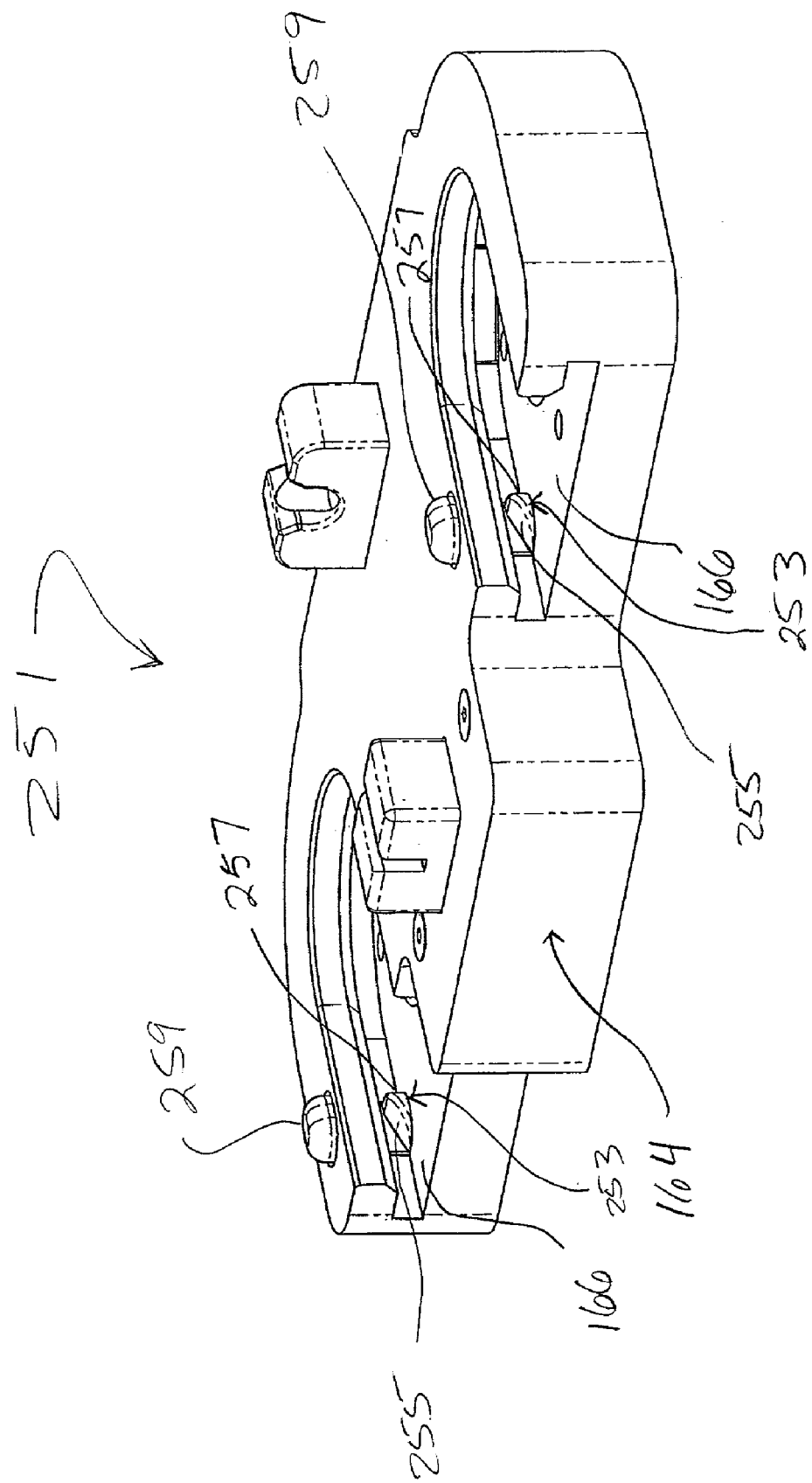
FIG. 15b is a perspective view of an alternative docking plate of the present invention; and, FIG. 16 is a flow diagram of the velocity loop and pressure loop of the present invention.

Another embodiment of a syringe locking device 251 is shown in FIGS. 2 and 4 and in detail in FIG. 15b. The syringe locking device 251 is mounted on the same or similar docking plate 164. It employs one catch 253 associated with each groove 166. The catch 253 is an upwardly biased protuberance having an angled edge 255 that allows the catch 253 to be pressed downwardly when the flange 234 of the syringe 44 passes over the catch 253. A substantially vertical edge 257 prevents the syringe 44 from retreating out of the groove 166 once the syringe 44 is fully inserted into the groove 166 and the catch 253 has snapped back into an engaged position. A release button 259 allows the operator to depress the catch 253 so that the syringe 44 may be removed.

Referring back to FIGS. 4 and 7-9, there is shown a linear position sensor 170. The linear position sensor 170 includes a stationary rod 172 and a position detector 174 that rides on the guide flange 144 in close proximity to the stationary rod 172. The position sensor 170 further includes a communications port 176 for relaying position data to the local control panel 94. The operation of the position sensor 170 will be discussed in more detail below. Acceptable position sensors include magnetostrictive position sensors such as Temposonics® commercial sensors manufactured by MTS® Systems Corporation at Cary, N.C.

Figure 11:
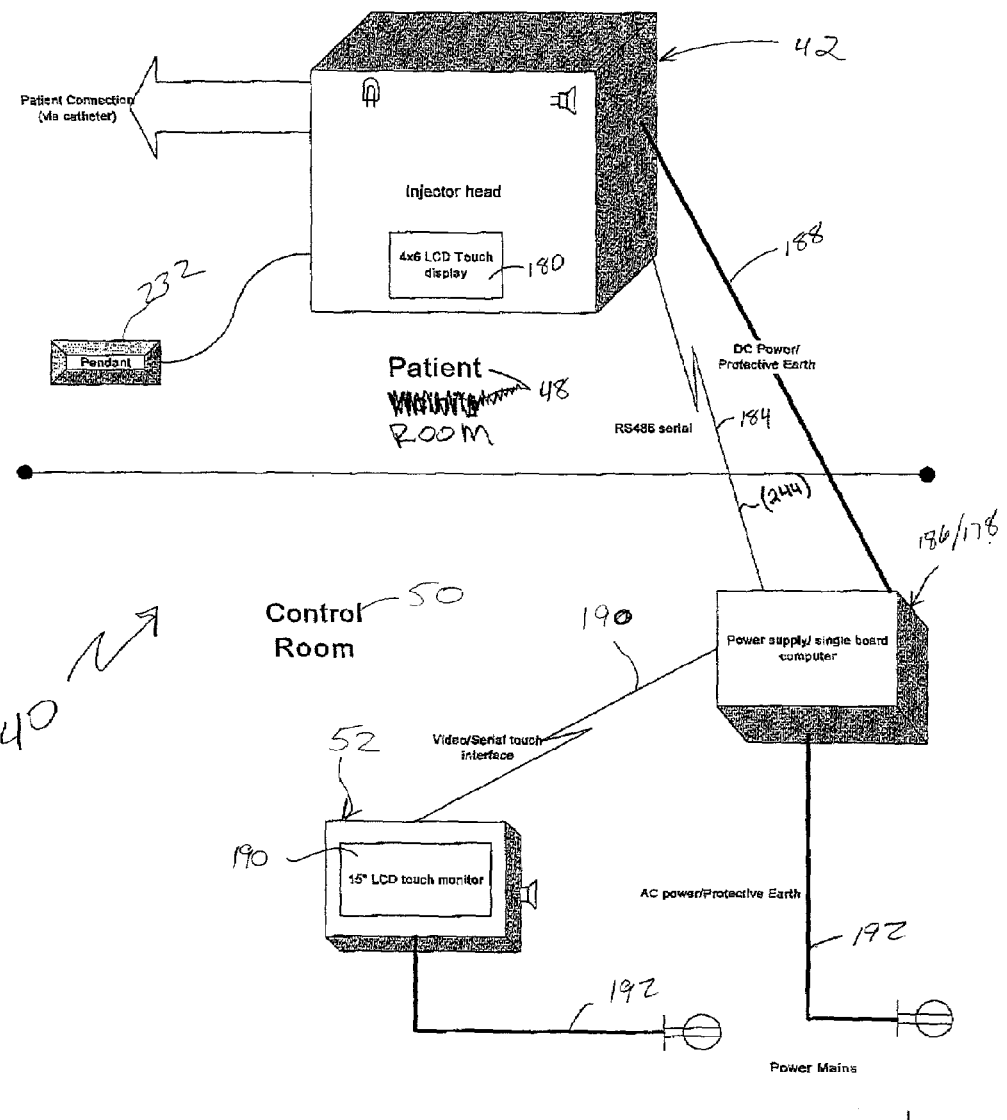
FIG. 11 is a diagram of the basic components of the automatic injector system of the present invention.

As shown diagrammatically in FIG. 11, the injector head 42 also includes a local control panel 94. The local control panel is basically a computer 178 with an interface 180 for manipulating the software programs that control the motors 110. A transceiver (not shown) operably connected to the computer 178 allows the injector head 42 to communicate with the remote operating panel 52.

The injector head 42 is shown in the patient room 48. A communications link 184 is established between the transceiver (not shown) inside the injector head 42 and the computer 178, which is located in the control room 50. Preferably, there is a computer 178 in both rooms. The computer 178 in the patient room 48 is considered part of the injector head 42. The injector head 42 also receives direct current power from a power supply 186 (shown as integral with the computer 178) via a grounded power line 188. A pendant 232 is also located in the patient room 48. The pendant 232 is a tethered on/off switch attached to the local control panel 94. The pendant 232 allows the operator to turn the system 40 on and off while verifying proper fluid flow using the method 10.

Also located in the control room 50 is the remote operating panel 52 that establishes a communications link 190 with the computer 178. The remote operating panel 52 preferably includes a touch monitor 190. Both the remote operating panel 52 and the power supply 186 have power mains 192 that receive alternating current power from outlets in the control room 50.

Injector Head Operation

Figure 12:
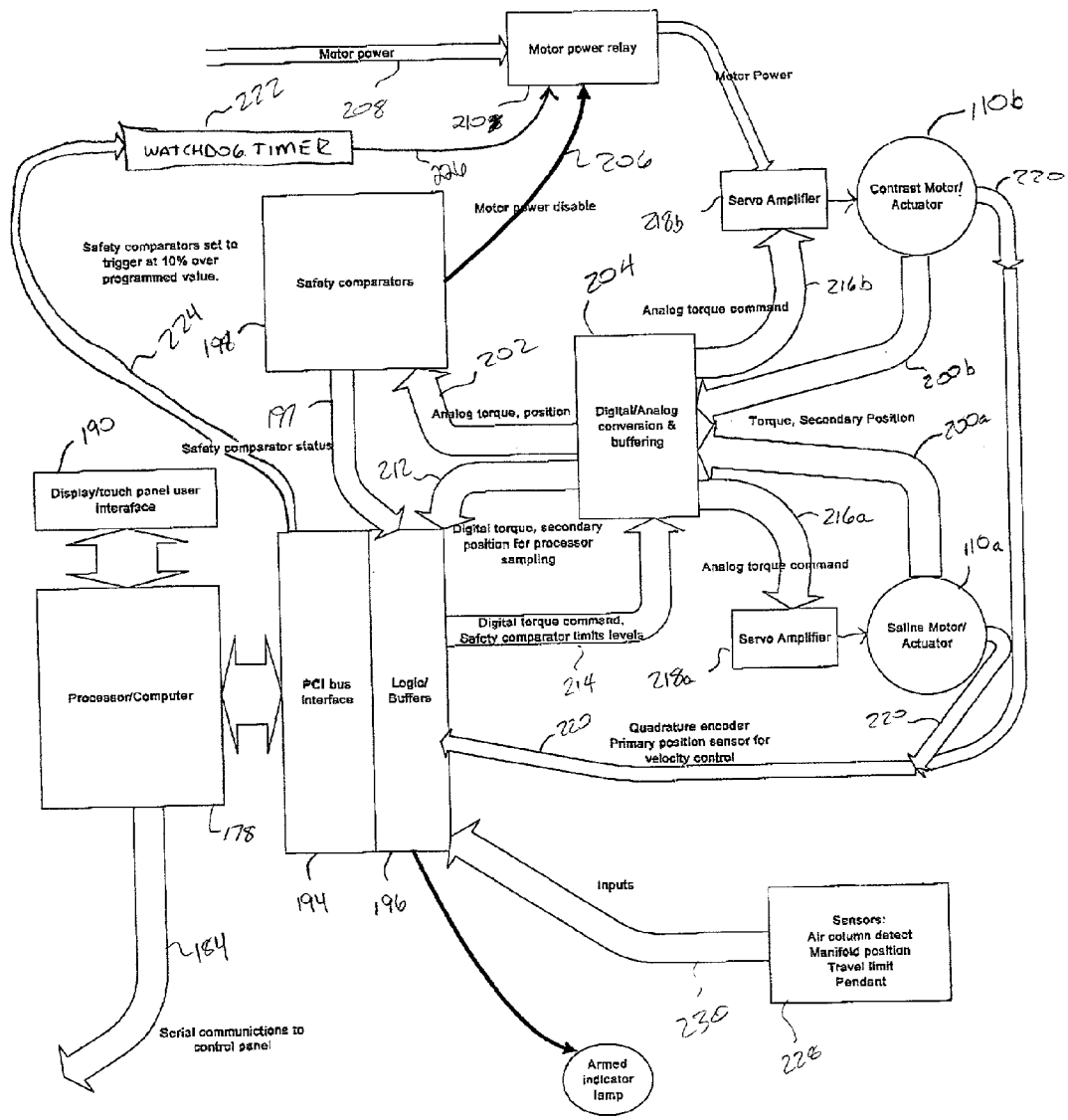
FIG. 12 is a data flow diagram of the injector head operation of the present invention.

The overall data flow operation of the injector head 42 is diagrammed in FIG. 12. The diagram introduces many of the safety features of the present invention. An overview explanation of FIG. 12 will be followed by a detailed analysis of these features.

Beginning with the processor 178, it can be seen that data flows to and from the other components in the system via a peripheral component interconnect (PCI) bus interface 194 that includes memory designated to store logic and act as a buffer 196. The computer 178 is also in electronic communication with the touch monitor 190 of the remote operating panel 52. The computer sends the appropriate commands via the communications link 184 to the local control panel 94 (FIGS. 2 and 4).

The PCI bus interface 194 provides the interconnect for all of the various components to communicate with each other. Starting at the top of the diagram and working clockwise it can be seen that data 197 is received by the buffers 196 from the safety comparators 198. These comparators are part of a software-based safety feature that automatically set a safety limit at a predetermined margin, e.g. on the order of 10%, above a parameter entered by the operator. The buffered data 202 that the comparators monitor originates as data 200a and 200b obtained from sensors on the motors 110a (saline) and 110b (contrast agent). Data 200a and 200b first undergoes digital/analog conversion and buffering at 204. The data 200a and 200b includes motor torque and position and is measured or computed by sensors that will be discussed in more detail below. If the buffered data 202 exceeds 110% of the entered parameters, the safety comparator 198 may send a signal 206 that disables the power 208 to the motors by tripping the motor power relay 210.

In addition to providing buffered analog data 202 to the safety comparators 198, the digital/analog conversion and buffering process 204 supplies digital data 212 directly to the buffers 196. This digital information 212 pertaining to the motors 110 is used by the computer 178 as feedback on whether the motors 110 are performing as expected. If the computer 178 determines adjustments need to be made, digital commands 214 are converted to analog signals at 204 and sent as commands 216 to the appropriate servo amplifiers 218, which then send corrected direct current power to the motor 110.

In addition to the sensors providing the torque and secondary position data 200 from the motors 110, the motors also have quadrature encoders 182 (FIG. 14) providing primary position data 220 for plunger velocity control. This data 220 is also received by the processor 178 via the buffers 196. Like the sensors, these encoders 182 will be discussed in detail below.

To prevent a computer problem, such as a single circuit failure, from adversely affecting the operation of the motors 110, a watchdog timer 222 is provided that receives reset signals 224 from the processor 178 via the PCI bus interface 194. The watchdog timer 222 is part of a watchdog safety feature that will be discussed individually. The timer 222, like the comparators 198, is able to send a motor power shutdown signal 226 to the motor power relay 210.

Other sensors and devices 228 may also provide inputs 230 to the computer 178 via the buffers 196. Examples of such inputs 230 include: air column alert, manifold position, travel limits, and pendant commands. An air column detector may be fashioned to the catheter connector 68 such that if an air column develops in the line leading to the catheter, the motors 110 may be stopped to prevent injecting air into the patient. Manifold position and travel limits are obtained from the linear position sensor 170. The individual safety features and components will now be discussed.

Watchdog Feature

Figure 13:
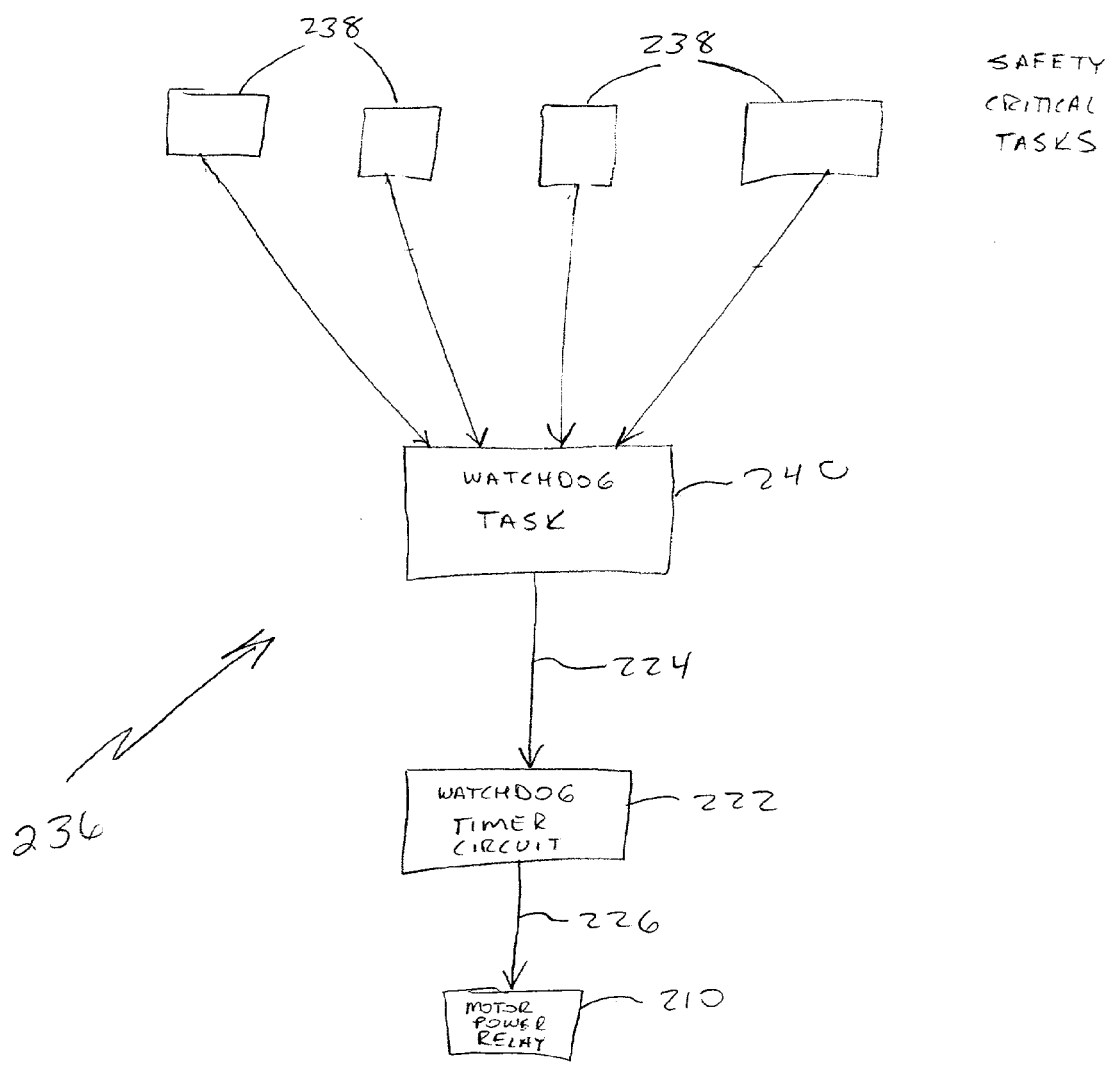
FIG. 13 is a flow diagram of the watchdog feature of the present invention.

Referring to FIG. 13, the watchdog feature 236 of the present invention is diagrammed. The watchdog feature 236 includes the aforementioned watchdog timer circuit 222 and motor power relay 210, and also includes a watchdog task 240 that monitors a plurality of safety-critical tasks 238. The watchdog feature 236 is a software-driven safety feature that ensures all of the software tasks 238, deemed safety-critical, are operating normally. The safety-critical tasks 238 are those programs or subprograms that operate continuously during an injection and could adversely affect safety if they malfunction.

The watchdog task 240 is a code segment that takes "roll call". At a predetermined interval, it determines if all of the safety-critical tasks 238 are operating normally. It preferably does this passively, requiring that each of the tasks 238 "check in". If all of the tasks 238 report a normal operating status within the predetermined interval, the watchdog task sends a timer reset signal 224 to the watchdog timer circuit 222 resetting the timer 222 to zero. The watchdog timer circuit 222 is a timer circuit that continually runs or advances until a predetermined time is achieved. Once the predetermined time is achieved, the timer circuit sends the motor power shutdown signal 226 to the motor power relay 210, tripping the relay 210 and cutting power to the motors 110. As long as the watchdog task 240 sends reset signals 224 to the watchdog timer circuit 222 before the timer circuit 222 reaches the predetermined time, the timer circuit will not send the motor power shutdown signal 226 to the motor power relay 210.

Interprocessor Communications Link

One of the safety-critical tasks 238 is an interprocessor communications link 244 (FIG. 11). The interprocessor communications link is signal sent over the communications link 184 between the processors 178 of the injector head 42 and the remote operating panel 52. The two microprocessors 178 communicate with each other by sending pings back and forth at a predetermined interval. These pings indicate that each processor 178 is operating normally. At each interval, if normal operations have been confirmed, a corresponding signal is sent to the watchdog task 240 that the watchdog task 240 acknowledges as one of the necessary signals for a successful roll call before resetting the watchdog timer 222.

Further safety may be provided by encoding the pings between the microprocessors 178. Changing the code at each interval according to a predetermined schedule may prevent one of the processors 178 from sending a false positive ping.

Quadrature Encoders

Figure 14:
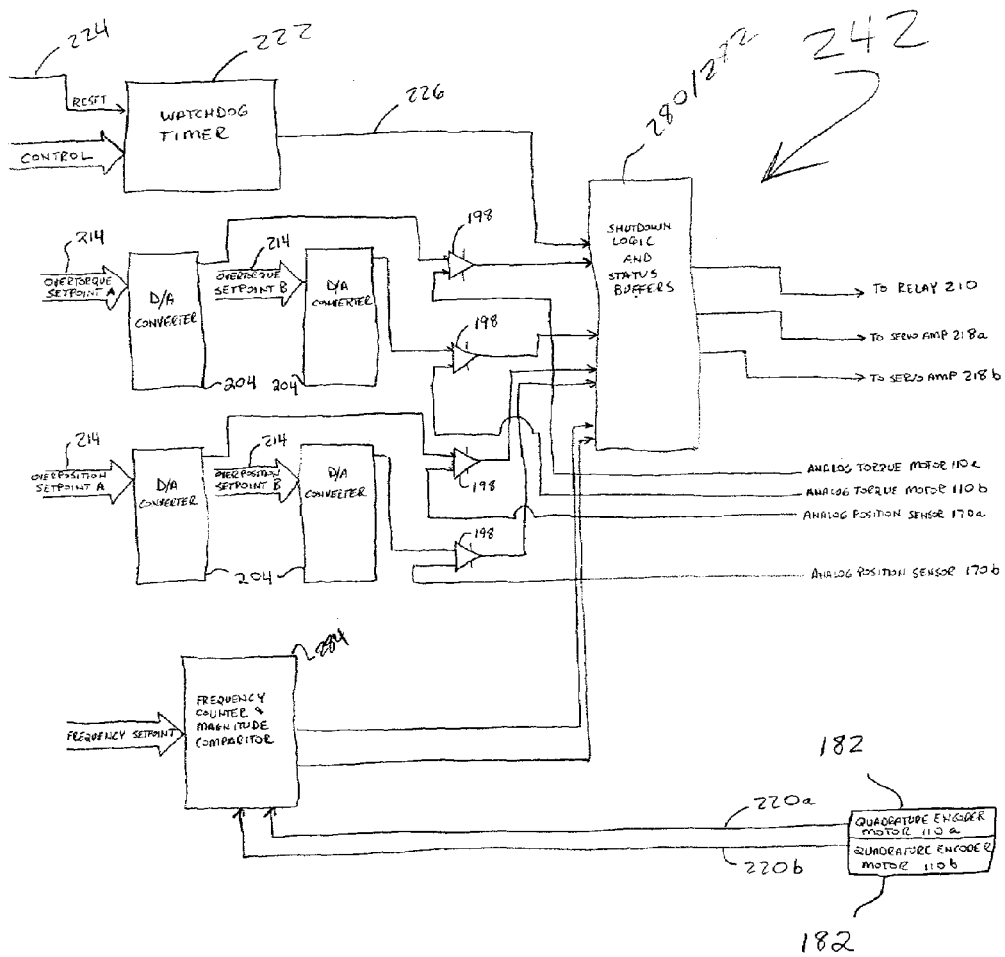
FIG. 14 is a logic flow diagram of the safety circuit of the present invention.

The motors 110 are equipped with quadrature encoder 182 (FIG. 14). Quadrature encoder 182 are known sensors that include a stationary pickup in operable proximity to two flags, such as magnets, on a moving (in this case rotating) part. The flags are 90 degrees apart on the rotor of the motor 110 to create two sine waves or digital "square wave" pulse signals that are 90 degrees out of phase and distinguishable from each other. By monitoring the digital pulse signals, rotor speed and position can be calculated from the frequency of the pulses and the total number of the pulses, respectively. By monitoring two sets of pulses that are out of phase, rotor direction can be determined by detecting which wave is leading the other wave. Summing the number of pulses in one direction, and subtracting from the total the pulses occurring while the rotor is traveling in the opposite direction, the linear position of the plunger rod 90 can be calculated.

As noted in FIG. 12, digital quadrature encoder data 220 is generated by each motor 110 and sent to the processor 178 via the buffer 196 and PCI bus interface 194. The processor 178 makes the calculations to determine the position and velocity of the plunger rod 90. Notably, if a computer problem results in a loss of the flag count, rod position can no longer be calculated unless the rod 90 is moved to a zero position and the counter is reset.

Analog Data

Also introduced in FIG. 12, analog data 200 pertaining to motor torque and plunger rod position flows to the safety comparators 198 and to the processor 178. The analog position data is obtained from the linear position sensor 170, shown in FIG. 9 and described above. This analog position data provides safety redundancy to the digital position data generated by the processor 178 using inputs from the quadrature encoder 182 on the motors 110. The linear position sensor 170 senses absolute position and, therefore, does not have to be reset.

The analog torque data is simply a measure of the current draw by the motors. Current draw provides an accurate indication of resistance to rotation. An increase in current draw, for any given flow rate, may be indicative of a problem such as a clog in the fluid communication network 46, a mechanical problem within the motor 110, or the possibility that the end of the catheter has abutted against the interior wall of the vessel into which it is inserted.

Safety Circuit

FIG. 14 shows an embodiment of the overall safety circuit 242 used by the computer 178 to prevent unsafe conditions. Limits 214 pertaining to torque and plunger rod position for both motors 110a and 100b are entered into the computer 178 and are stored in the buffer 196 (FIG. 12). When summoned, the limits 214 pass through the digital to analog converters 204 so they may be read by the analog comparators 198. The comparators 198 compare actual readings for torque (current draw) and rod position (read from the linear position sensor 170) to the converted limits and feed digital (true/false) results to a status buffer 282. The comparators 198 are programmed to add a predetermined percentage or constant to the inputted limit to allow for inaccuracies in the system, thereby preventing unwanted false shutdowns. The status buffer is in data flow communication with a shutdown logic program 280, detailed below. The status buffer 282 may be the same buffer as buffer 196.

In addition to the output from the comparators 198, the shutdown logic program 280 receives inputs via buffer 282 from the frequency counter and magnitude comparator 284. The frequency counter measures the encoder 182 pulse frequency by recording the amount of time between pulses (the period of the pulses). The period is inversely proportional to the frequency of the pulses and the flow rate of the injectate. The magnitude comparator detects when this frequency has exceeded a predetermined set point value. The digital output of the frequency counter 284 is stored in the status buffers 282 for use by the computer 178 to monitor the speed and positions of the plungers 74.

The shutdown logic program 280 operates by monitoring the results from the comparators 198 and shutdown signals 226 from the watchdog timer 222. If the shutdown logic program 280 receives a signal from any of the comparators 198 indicating that a limit has been exceeded, or a signal 226 from the watchdog timer 222 indicating that one of the safety-critical tasks has encountered an error, a trip signal is sent to the motor relay 210, cutting power to both motors 110.

Velocity Loop/Pressure Loop Program

Figure 16:
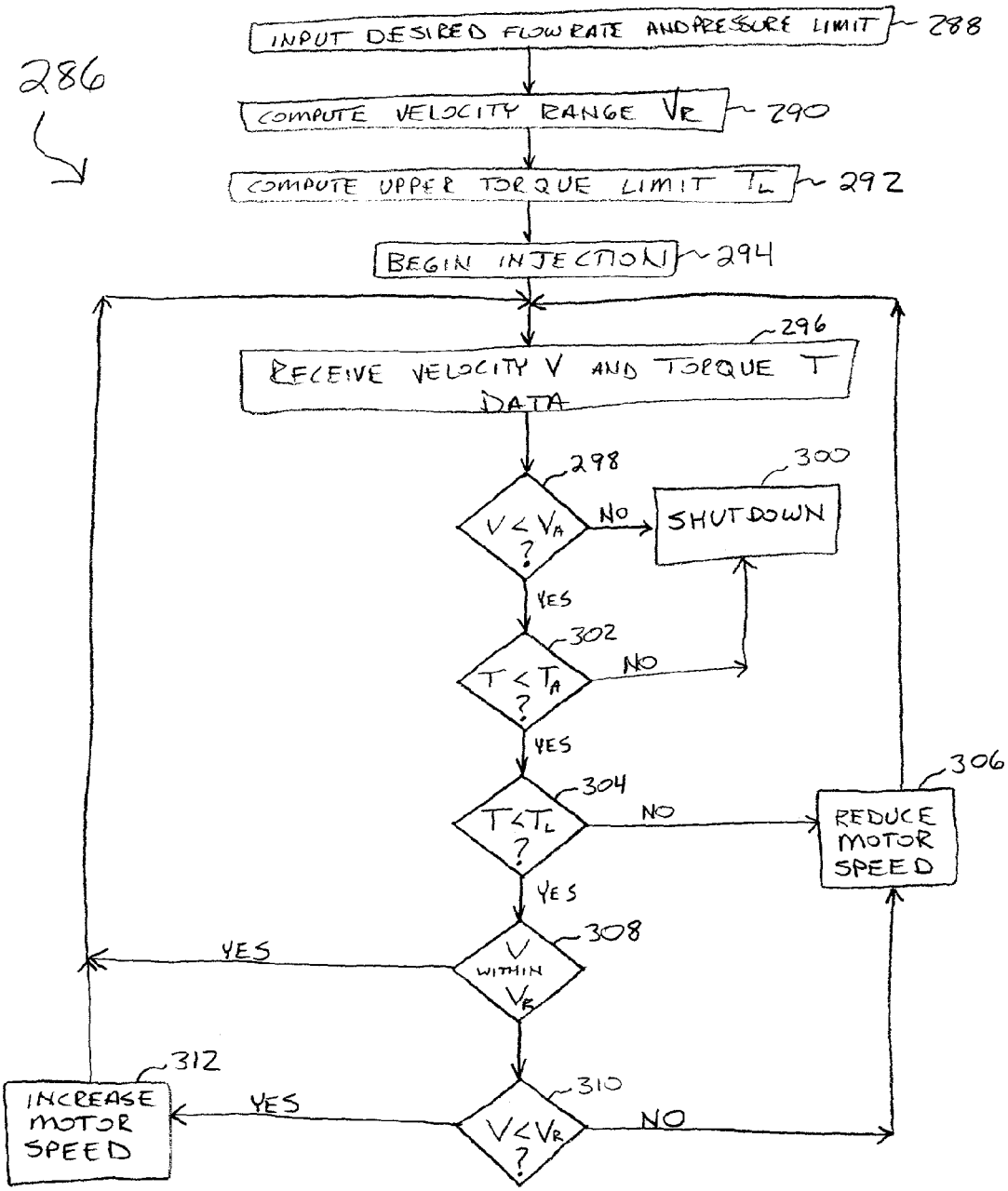

FIG. 16 is a flow chart of how the computer 178 maintains the desired injectate flow rate during an injection. To maximize the efficacy of the contrast agent, an optimal volume of contrast agent must be flowing through the area of the body being imaged. Thus, a predetermined flow rate is maintained using motor speed. However, if the motor is hindered from rotation, such as due to a clog or a mechanical malfunction, the motor speed should be decreased to prevent harm to the patient or equipment. The program 286 charted in FIG. 16 maintains a desired flow rate without exceeding an upper pressure limit.

The velocity loop/pressure loop program 286 begins at 288 with the operator entering the desired injectate flow rate and upper pressure limit. At 290 the computer 178 calculates the motor speed that corresponds to the desired flow rate based on the cross-sectional area of the syringe 44, the pitch of the plug screw 120, and the reduction ratio of the motor gear 116 to the plug screw gear 118. The computer also adds a tolerance around the computed motor speed to generate an acceptable velocity range, $V_R$. The computer has preset upper absolute limits on velocity and change in velocity, $V_A$, and torque and change in torque, $T_A$. For simplicity, the absolute velocity limit and limit on change in velocity are both denoted as $V_A$. The same convention is true for torque and change in torque.

Next, at 292, the computer 178 calculates the upper torque limit $T_L$ based on the inputted upper pressure limit. The operator, when selecting the upper pressure limit, considers the viscosity of the fluid. The pressure limit should be set higher for more viscous liquids for a given flow rate. The computer 178 allows for resistance to flow due to the friction inherent in the mechanical system 40. Torque, as discussed above, is calculated as a function of motor current draw.

At 294 the injection begins. At 296, as a liquid is being injected, the computer 178 receives continuous velocity readings from the quadrature encoder 182 (FIG. 14) of the operating motor 110. The computer 178 is also receiving torque data representing the current drawn by the operating motor 110. The computer 178 is not only noting the velocity V and the torque T, but also the rate of change of velocity and torque.

At 298, the computer 178 first checks to ensure the absolute limits on velocity and change in velocity, $V_A$, are not exceeded. Exceeding these limits, $V_A$, indicates a probable hardware or software failure resulting in an inability to control the motor. Thus, if $V_A$, is exceeded, the computer sends a trip signal at 300, which trips the motor power relay 210.

At 302, the computer 178 checks to ensure the absolute limits on torque and change in torque, $T_L$, are not exceeded. If exceeded, the computer sends the trip signal 300 to the motor power relay 210. Excessive torque and an abrupt change in torque are indicative of a clog or mechanical failure and warrant a shutdown signal.

At 304, the computer 178 is comparing the actual torque T to the computed torque limit $T_L$. If the actual torque T exceeds the limit, the motor speed is reduced at 306.

At 308, if the torque limit $T_L$ is not exceeded, the computer 178 determines whether the actual velocity V is within the acceptable velocity range, $V_R$. If it is, the injection continues at the present motor speed and computer continues to monitor torque T and velocity V at 296. If the velocity V is not within the acceptable velocity range $V_R$, the computer 178 determines whether the velocity V is too high or too low at 310. If the velocity V is too low, the motor speed is increased at 312. If the velocity V is too high, the motor speed is decreased at 306.

This program 286 operates independently from the circuit 242. Thus, an overtorque situation could result in a shutdown generated by circuit 242, or by the program 286. However, controlling torque by decreasing motor speed is performed only by the program 286. Importantly, the independence of these two programs, 286 and 242, provides a degree of redundancy to the safety of the operation of the system 40.

Modular Memory

To provide enhanced flexibility, and minimize downtime in the event of software problems, the above programs and buffers may be provided on a modular memory card 245. Referring to FIG. 2, it can be seen that a mass storage device in the form of a modular memory card 245, such as CompactFlash™, is provided on both the local control panel 94 and the remote operating panel 52. The modular memory cards 245 can be unplugged and replaced through an access point on the injector device. Using these cards 245 to store application software, calibration data, and device usage data, provides the ability to both download and retrieve the software and data from the injector using a connected computer, and to physically remove and replace the cards 245 containing data.

The foregoing description addresses embodiments encompassing the principles of the present invention. The embodiments may be changed, modified and/or implemented using various types of arrangements. Those skilled in the art will readily recognize various modifications and changes that may be made to the invention without strictly following the exemplary embodiments and applications illustrated and described herein, and without departing from the scope of the invention, which is set forth in the following claims.

What is claimed is:

1. An injectate delivery device comprising:
   first and second syringes each having a distal end;
   a catheter connector attachable to a percutaneous implement;
   a fluid communication network, fluidly connecting the distal ends of the first and second syringes to the catheter connector, the network including a shuttle valve constructed and arranged to selectively port fluid from one of the first and second syringes to the catheter connector while blocking fluid from the other of the first and second syringes, wherein the shuttle valve comprises:
   a housing defining a common inner chamber and three connection openings, at least two of the connection openings fluidly leading into the common inner chamber through passageways narrower than the common inner chamber, and defined by shoulders extending inwardly from the housings
   two plugs, each having a diameter smaller than that of the common inner chamber and larger than that of the passageways, the plugs and shoulders constructed and arranged such that the plugs form seals against the respective shoulders when the plugs are pressed there against;
   a common biasing mechanism contained within the common inner chamber and constructed and arranged such that the plugs are forced against their respective shoulders by the common biasing mechanism, thereby forming a seal there against, unless one of the plugs is overcome by fluid pressure from one of the syringes, being forced inwardly, away from its respective shoulder, thereby allowing fluid to flow from the pressure-providing syringe, and into the catheter connector.

2. The device of claim 1 further comprising a first supply connector fluidly coupleable to the first syringe.

3. The injectate delivery device of claim 2 further comprising a coupling between said first supply connector and said first syringe, useable to disconnect said first supply connector from said first syringe.

4. The device of claim 2 wherein the first supply connector is fluidly coupleable to the distal end of the first syringe.

5. The device of claim 2 further comprising a check valve fluidly coupling the first supply connector to the first syringe.

6. The device of claim 5 wherein the check valve further fluidly couples the first syringe to the shuttle valve.

7. The injectate delivery device of claim 6 further comprising a coupling between said check valve and said shuttle valve, useable to disconnect said check valve from said shuttle valve.

8. The device of claim 5 wherein the check valve is constructed and arranged such that the valve is biased toward a closed position whereby the fluid connection between the first syringe and the first supply connector is blocked and whereby a predetermined negative pressure in said first syringe, relative to the static fluid pressure in the first supply connector, is required to cause the valve to assume an open position, whereby fluid is able to be drawn into the first syringe from a first fluid supply reservoir operably attached to the first fluid supply connector.

9. The device of claim 8 wherein the check valve comprises:
- a tubular housing, attachable at one end to the distal end of the first syringe, defining an inner lumen; a plug contained within the inner lumen, the plug having a diameter smaller than an inner diameter of the lumen such that fluid may pass around the plug;
- a narrowed section extending inwardly from another end of the housing to define a narrow passage having an inner diameter smaller than the diameter of the plug, the narrowed section thereby forming an inner shoulder against which the plug may rest and form a seal preventing fluid from flowing from the first syringe to the narrow passage;
- a biasing mechanism contained within the inner lumen, biased to hold the plug against the shoulder until the biasing mechanism is overcome by a predetermined negative pressure in the first syringe, relative to the static fluid pressure in the first supply connector, whereby the plug is drawn away from the shoulder, thereby allowing fluid to flow from the supply connector into the first syringe.

10. The device of claim 1 further comprising a second supply connector fluidly coupleable to the second syringe.

11. The device of claim 10 wherein the second supply connector is fluidly coupleable to the distal end of the second syringe.

12. The injectate delivery device of claim 10 further comprising a coupling between said second supply connector and said second syringe, useable to disconnect said first supply connector from said first syringe.

13. The device of claim 10 further comprising a second check valve fluidly coupling the second supply connector to the second syringe.

14. The device of claim 13 wherein the second check valve further fluidly couples the second syringe to the shuttle valve.

15. The injectate delivery device of claim 14 further comprising a coupling between said second check valve and said shuttle valve, useable to disconnect said check valve from said shuttle valve.

16. The device of claim 13 wherein the check valve is constructed and arranged such that the valve is biased toward a closed position whereby the fluid connection between the second syringe and the second supply connector is blocked and whereby a predetermined negative pressure in said second syringe, relative to the static fluid pressure in the second supply connector, is required to cause the valve to assume an open position, whereby fluid is able to be drawn into the second syringe from a second fluid supply reservoir operably attached to the second fluid supply connector.

17. The device of claim 16 wherein the check valve comprises:
- a tubular housing, attachable at one end to the distal end of the second syringe, defining an inner lumen;
- a plug contained within the inner lumen, the plug having a diameter smaller than an inner diameter of the lumen such that fluid may pass around the plug;
- a narrowed section extending inwardly from another end of the housing to define a narrow passage having an inner diameter smaller than the diameter of the plug, the narrowed section thereby forming an inner shoulder against which the plug may rest and form a seal preventing fluid from flowing from the second syringe to the narrow passage;
- a biasing mechanism contained within the inner lumen, biased to hold the plug against the shoulder until the biasing mechanism is overcome by a predetermined negative pressure in the second syringe, relative to the static fluid pressure in the second supply connector, whereby the plug is drawn away from the shoulder, thereby allowing fluid to flow from the supply connector into the second syringe.

18. The injectate delivery device of claim 1 further comprising a coupling between said catheter connector and said shuttle valve, useable to disconnect said catheter connector from said shuttle valve.

19. The injectate delivery device of claim 1 wherein the biasing mechanism of the shuttle valve comprises a spring to hold apart the two plugs of the shuttle valve.

20. The injectate delivery device of claim 1 wherein the two plugs of the shuttle valve are located at substantially opposite ends of the biasing mechanism.

* * * * *